US010718032B2

(12) United States Patent
Perez Diaz et al.

(10) Patent No.: US 10,718,032 B2
(45) Date of Patent: Jul. 21, 2020

(54) METHODS AND COMPOSITIONS TO EVALUATE AND DETERMINE INACTIVATION OF HAZARDOUS BIOLOGICAL MATERIAL

(71) Applicants: THE UNITED STATES OF AMERICA, AS REPRESENTED BY THE SECRETARY OF AGRICULTURE, Washington, DC (US); NORTH CAROLINA STATE UNIVERSITY, Raleigh, NC (US)

(72) Inventors: Ilenys M. Perez Diaz, Raleigh, NC (US); Jane M. Caldwell, Storm Lake, IA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 860 days.

(21) Appl. No.: 14/917,830

(22) PCT Filed: Sep. 9, 2014

(86) PCT No.: PCT/US2014/054749
§ 371 (c)(1),
(2) Date: Mar. 9, 2016

(87) PCT Pub. No.: WO2015/038526
PCT Pub. Date: Mar. 19, 2015

(65) Prior Publication Data
US 2016/0222437 A1 Aug. 4, 2016

Related U.S. Application Data

(60) Provisional application No. 61/876,425, filed on Sep. 11, 2013, provisional application No. 61/969,465, filed on Mar. 24, 2014.

(51) Int. Cl.
*C12Q 1/68* (2018.01)
*C12Q 1/689* (2018.01)
*C12Q 1/6888* (2018.01)

(52) U.S. Cl.
CPC ........... *C12Q 1/689* (2013.01); *C12Q 1/6888* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,871,563 A | 10/1989 | Tatini | |
| 5,486,459 A | 1/1996 | Burnham et al. | |
| 5,830,683 A | 11/1998 | Hendricks et al. | |
| 2002/0176895 A1* | 11/2002 | Goswami | C09B 61/00 424/520 |
| 2007/0111227 A1* | 5/2007 | Green | C12N 15/111 435/6.13 |
| 2007/0249040 A1 | 10/2007 | Miyamoto et al. | |
| 2008/0276334 A1* | 11/2008 | Abad | C07K 14/415 800/287 |
| 2011/0223598 A1 | 9/2011 | Opdyke et al. | |
| 2012/0231461 A1* | 9/2012 | Allawi | C12Q 1/6816 435/6.11 |

FOREIGN PATENT DOCUMENTS

WO 9508639 A1 3/1995
WO WO 2007092279 A2 * 8/2007

OTHER PUBLICATIONS

Teoh et al, FEBS Lett. 580 (5), 1411 (2006).*
Andreas et al, Plant Physiol. 144 (1), 32 (2007).*
Fukuoka et al, Gene 450 (1-2), 76 (2010).*
Tanase et al, BMC Genomics 13, 292 (2012).*
Emrich et al, Genome Res. 17 (1), 69 (2007).*
Narina et al, BMC Genomics 12, 100 (2011).*
Qi et al, Nature 443 (7114), 1008 (2006).*
Adams J.B. et al.; "Nitrophenyl glucoside hydrolysis as a potential time-temperature integrator reaction", (1998), Food Chemistry, 62(1):65-68.
Abdreasson, H. et al.; "Real-Time DNA Quantification of Nuclear and Mitochondrial DNA in Forensic Analysis", (Aug. 2002), BioTechniques, 33:402-411.
Budowle, B. et al.; "Forensics and Mitochondrial DNA: Applications, Debates, and Foundations*", (2003), Annu. Rev Genomics Hum. Genet, 4:119-41.
Caldwell, J.M. et al., "Mitochondrial DNA as molecular indicators of thermal processing efficacy", (Apr. 2014), Capp Seed Final Report.
Caldwell, J.M. et al., "Mitochondrial Multiplex Real-Time PCR as a Source Tracking Method in Fecal-Contaminated Effluents", (2007), Environ. Sci. Technol., 41:3277-3283.
Caldwell, J., et al., "Mitochandrial DNA as Source Tracking Markers of Fecal Contamination", (2011), Ch. 10, 229-250.
Caldwell, J.M. et al., "Mitochondrial DNA Fragmentation as a Molecular Tool to Monitor Thermal Processing of Plant-Derived, Low-Acid Foods, and Biomaterials", Journal of Food Sci., (2015), 80(8): M1804-M1814.

(Continued)

*Primary Examiner* — James Martinell
(74) *Attorney, Agent, or Firm* — John Fado; Ariel Atkinson

(57) ABSTRACT

Novel time and temperature integrator (TTI) assays, kits containing the components of the assays, and the novel components for those assays are provided herein. These novel TTI assays evaluate and/or determine the inactivation of biological material in/on a sample by quantifying the degradation of DNA using qPCR. The sample can be a food product (e.g., fruits, vegetables, meat from animals, or eggs) while the item can be any object (e.g., medical equipment, especially reusable medical equipment) for which one needs to determine that the amount of inactivation of specific hazardous biological material on the object or in a sample is at or below a pre-determined amount.

27 Claims, 19 Drawing Sheets

Specification includes a Sequence Listing.

(56) References Cited

OTHER PUBLICATIONS

Caldwell, J.M. et al., "Mitochondrial DNA Fragmentation to Monitor Processing Parameters in High Acid, Plant-Derived Foods", Journal of Food Sci., (2015), 80(12): 2892-2898.

Choi et al., "Improved Detection of Viable *Escherichia coli* O157:H7 in Milk by Using Reverse Transcriptase-PCR", Korean J. Food Sci. Ani. Resour., (2011) 31(2): 158-165.

Caldwell, J.M. et al., "Domestic wastewater influent profiling using mitochondrial real-time PCR for source tracking animal contamination", Journal of Microbiological Methods, (2009), 77:17-22.

Cordt, S.F. et al., "Convenience of Immobilized Bacillus licheniformis a-Amylase as Time-Temperature-Integrator (TTI)", J. Chem. tech. Biotechnol. (1994), 59:193-199.

Galan, A.M-G et al., "Development of a real-time PCR method for the simultaneous detection of soya and lupin mitochondrial DNA as markers for the presence of allergens in processed food", Food Chemistry, (2011) 127:834-841.

Gryson, N., "Effect of food processing on plant DNA degradation and PCR-based GMO analysis: a review", Anal Bioanal Chem., (2010), 396:2003-2022.

Hopwood, A.J., et al., "DNA typing from human faeces", Int. J. Legal Med, (1996) 108:237-243.

Hyeon et al., Evaluation of an Automated ELISA (VIDAS®) and Real-time PCR by Comparing with a Conventional Culture Method for the Detection of Salmonella spp. in Steamed Pork and Raw Broccoli Sprouts, Korean J. Food Sci. Ani Resour., (2009), 29(4): 506-512, Abstract Only.

Hyeon et al., "Development of multiplex real-time PCR with Internal amplification control for simultaneous detection of Salmonella and Cronobacter in powdered infant formula", Int. Journal of Food Microbiology, (2010), 144:177-81.

Jackson et al., "qPCR-based mitochondrial DNA quantification: Influence of template DNA fragmentation on accuracy", Biochemical and Biophysical Research Communications, (2012), 423:441-447.

Lahiff, S. et al., "Species-specific PCR for the identification of ovine, porcine and chicken species in meat and bone meal (MBM)", Molecular and Celluar Probes, (2001), 15:27-35.

Lee, S.H. et al., "A multiplex real-time PCR for differential detection and quantification of Salmonella spp., Salmonella enterica serovar Typhimurium and Enteritidis in meats", Journal of Veterinary Science, (2009), 10(1):43-51.

Lipp, M. et al., "IUPAC Collaborative Trial Study of a Method to Detect Genetically Modified Soy Beans and Maize in Dried Powder1", Journal of AOAC International, (1999), 82(4):923-928.

Lipp, M. et al., "Validation of an Immunoassay for Detection and Quantitation of a Genetically Modified Soybean in Food and Food Fractions Using Reference Materials: Interlaboratory Study", Journal of AOAC International, (2000), 83(4): 919-928.

Meyer, R. et al., "PCR-based DNA Analysis for the Identification and Characterization of Food Components", Lebensm.-Wiss. u.-Technol., (1996), 29:1-9.

Moreano, F. et al., "Distortion of Genetically Modified Organism Quantification in Processed Foods: Influence of Particle Size Compositions and Heat-Induced DNA Degradation", J. Agric. Food Chem., (2005), 53:9971-9979.

Murray, S.R. et al., "Use of Quantitative Real-Time PCR to Estimate Maize Endogenous DNA Degradation after Cooking and Extrusion or in Food Products", J. Agric. Food Chem., (2007), 55:2231-2239.

Postollec, F. et al., "Recent advances in quantitative PCR (qPCR) applications in food microbiology", Food Microbiology, (2011), 28: 848-861.

Sakalar, E. et al., "Effect of Heat Processing on DNA Quantification of Meat Species", Journal of Food Science, (2012), 77(9):40-44.

Stam, C. N., Development of Novel Biological Indicators to Evaluate the Efficacy of Microwave Processing. (Under the direction of Dr. Lee-Ann Jaykus), (2008), Thesis, pp. 1-166.

Zhang, C-L. et al., "A TaqMan real-time PCR system for the identification and quantification of bovine DNA in meats, milks and cheeses", Food Control, (2007), 18:1149-1158.

* cited by examiner

```
               1
108F           ------------ ------------ ------------ ------------ ------------ ------------
Ipomoea batatas TGGATGAGAT CGGTCGAGTG GTCTCAGTTG GAGATGGGAT TTCACGTGTT TATGGATTGA  SEQ ID NO: 9
174F           ------------ ------------ ------------ ------------ ------------ ------------
81F            ------------ ------------ ------------ ------------ ------------ ------------
141F           ------------ ------------ ------------ ------------ ------------ ------------
174R           ------------ ------------ ------------ ------------ ------------ ------------
108R           ------------ ------------ ------------ ------------ ------------ ------------
81R            ------------ ------------ ------------ ------------ ------------ ------------
141R           ------------ ------------ ------------ ------------ ------------ ------------

61
108F           ------------ ------------ ------------ ------------ ------------ ------------
Ipomoea batatas ACGAGATTCA AGTGGGGAA ATGGTGGAT TTGCCAGCGG TGTGAAAGGA ATAGCCTTGA  SEQ ID NO: 9
174F           ------------ ------------ ------------ ------------ ------------ ------------
81F            ------------ ------------ ------------ ------------ ------------ ------------
141F           ----------- ----------- ------GAAT TTGCCAGCGG TGTGAAGGA -----------  SEQ ID NO: 7
174R           ------------ ------------ ------------ ------------ ------------ ------------
108R           ------------ ------------ ------------ ------------ ------------ ------------
81R            ------------ ------------ ------------ ------------ ------------ ------------
141R           ------------ ------------ ------------ ------------ ------------ ------------

121
108F           ------------ ------------ ------------ ------------ ------------ ------------
Ipomoea batatas ATCTTGAGAA TGAGAATGTA GGGATGTTG TCTTGGTAG TGATACTGCT ATTAAGGAAG  SEQ ID NO: 9
174F           ------------ ------------ ------------ ------------ ------------ ------------
81F            ------------ ------------ ------------ ------------ ------------ ------------
141F           ------------ ------------ ------------ ------------ ------------ ------------
174R           ------------ ------------ ------------ ------------ ------------ ------------
108R           ------------ ------------ ------------ ------------ ------------ ------------
81R            ------------ ------------ ------------ ------------ ------------ ------------
141R           ------------ ------------ ------------ ------------ ------------ ------------

181
108F           ------------ ------------ ------------ ------------ ------------ ------------
Ipomoea batatas GAGATCTTGT CAAGCGCACT GGATCTATTG TGGATGTTCC TGCGGGAAAG GCTATGCTAG  SEQ ID NO: 9
174F           ------------ ------------ ------------ ------------ ------------ ------------
81F            ------------ ------------ ------------ ------------ ------------ ------------
141F           ------------ ------------ ------------ ------------ ------------ ------------
174R           ------------ ------------ ------------ ------------ ------------ ------------
108R           ------------ ------------ ------------ ------------ ------------ ------------
81R            ------------ ------------ ------------ ------------ ------------ ------------
141R           ----------- ----------- ----TCTATTG TGGATGTTCC TGCGGGA----- -----------  SEQ ID NO: 13

241
108F           ------------ ------------ ------------ ------------ ------------ ------------
Ipomoea batatas GGGGTGTGGT CGACGCCTTG GGAGTACCTA TTGATGGAAG AGGGGCTCTA AGCGATCACG  SEQ ID NO: 9
174F           ------------ ------------ ------------ ------------ ------------ ------------
81F            ------------ ------------ ------------ ------------ ------------ ------------
141F           ------------ ------------ ------------ ------------ ------------ ------------
174R           ------------ ------------ ------------ ------------ ------------ ------------
108R           ------------ ------------ ------------ ------------ ------------ ------------
81R            ------------ ------------ ------------ ------------ ------------ ------------
141R           ------------ ------------ ------------ ------------ ------------ ------------

301
108F           ------------ ------------ ------------ ------------ ------------ ------------
Ipomoea batatas AGCGAAGACG TGTCGAAGTG AAAGCCCCTG GGATTATTGA ACTAAATCT GTGCACGAGC  SEQ ID NO: 9
174F           ------------ ------------ ------------ ------------ ------------ ------------
81F            ------------ ------------ ------------ ------------ ------------ ------------
141F           ------------ ------------ ------------ ------------ ------------ ------------
174R           ------------ ------------ ------------ ------------ ------------ ------------
108R           ------------ ------------ ------------ ------------ ------------ ------------
81R            ------------ ------------ ------------ ------------ ------------ ------------
141R           ------------ ------------ ------------ ------------ ------------ ------------
```

```
              721
108F          ---------- ---------- ---------- ---------- ---------- ----------
Ipomoea batatas CAATAATAAT CTATGATGAT CTTAGTAAAC AGGCCGTAGC ATATCGACAA ATGTCATTAT SEQ ID NO: 9
174F          C--------- ---------- ---------- ---------- ---------- ---------- SEQ ID NO: 1
81F           ---------- ---------- ---------- ---------- ---------- ----------
141F          ---------- ---------- ---------- ---------- ---------- ----------
174R          ---------- ---------- ---------- ---------- ---------- ----------
108R          ---------- ---------- ---------- ---------- ---------- ----------
81R           ---------- ---------- ---------- ---------- ---------- ----------
141R          ---------- ---------- ---------- ---------- ---------- ----------

781
108F          ---------- ---------- ---------- ---------- ---------- ----------
Ipomoea batatas TGTTACGCCG ACCACCAGGT CGTCAGGCTT TCCCAGGGGA TGTTTTTTAT TTACATTCCC SEQ ID NO: 9
174F          ---------- ---------- ---------- ---------- ---------- ----------
81F           ---------- ---------- ---------- ---------- ---------- ----------
141F          ---------- ---------- ---------- ---------- ---------- ----------
174R          ---------- ---------- ---------- ---------- ---------- ----------
108R          ---------- ---------- ---------- ---------- ---------- ----------
81R           ---------- ---------- ---------- ---------- ---------- ----------
141R          ---------- ---------- ---------- ---------- ---------- ----------

841
108F          ---------- ---------- ---------- ---------- ---------- ----------
Ipomoea batatas GTCTCTTAGA AAGAGCGGCT AAACGATCGG ACCAGACAGG CGCAGGTAGC TTGACCGCCT SEQ ID NO: 9
174F          ---------- ---------- ---------- ---------- ---------- ----------
81F           ---------- ---------- ---------- ---------- ---------- ----------
141F          ---------- ---------- ---------- ---------- ---------- ----------
174R          -------AGA AAGAGCGGCT AAACGATCGG A--------- ---------- ---------- SEQ ID NO: 10
108R          ---------- ---------- ---------- ---------- ---------- ----------
81R           ---------- ---------- ---------- ---------- ---------- ----------
141R          ---------- ---------- ---------- ---------- ---------- ----------

901
108F          ---------- ---------- ---------- ---------- ---------- ----------
Ipomoea batatas TACCCGTCAT TGAAACACAA GCTGGAGACG TATCGGCCTA TATTCCCACC AATGTGATCC SEQ ID NO: 9
174F          ---------- ---------- ---------- ---------- ---------- ----------
81F           ---------- ---------- ---------- ---------- ---------- ----------
141F          ---------- ---------- ---------- ---------- ---------- ----------
174R          ---------- ---------- ---------- ---------- ---------- ----------
108R          ---------- ---------- ---------- ---------- ---------- ----------
81R           ---------- ---------- ---------- ---------- ---------- ----------
141R          ---------- ---------- ---------- ---------- ---------- ----------

961
108F          ---------- ---------- ---------- ---------- ---------- ----------
Ipomoea batatas CCATTACTGA TGACAAATC TGTTTGGAAA CAGAGCTCTT TTATGCGGA ATTAGACCTG SEQ ID NO: 9
174F          ---------- ---------- ---------- ---------- ---------- ----------
81F           ---------- ---------- ---------- ---------- ---------- ----------
141F          ---------- ---------- ---------- ---------- ---------- ----------
174R          ---------- ---------- ---------- ---------- ---------- ----------
108R          ---------- ---------- ---------- ---------- ---------- ----------
81R           ---------- ---------- ---------- ---------- ---------- ----------
141R          ---------- ---------- ---------- ---------- ---------- ----------

1021
108F          ---------- ---------- ---------- ---------- ---------- ----------
Ipomoea batatas CTATTAACGT CGGCTTATCT GTCAGTCGCG TCGGGTCTGC CGCTCAGTTG AAAGCTATGA SEQ ID NO: 9
174F          ---------- ---------- ---------- ---------- ---------- ----------
81F           ---------- ---------- ---------- ---------- ---------- ----------
141F          ---------- ---------- ---------- ---------- ---------- ----------
174R          ---------- ---------- ---------- ---------- ---------- ----------
108R          ---------- ---------- ---------- ---------- ---------- ----------
81R           ---------- ---------- ---------- ---------- ---------- ----------
141R          ---------- ---------- ---------- ---------- ---------- ----------
```

Figure 9 (CONT.)

```
            1081
108F                                                                            --CGCCTTTG SEQ ID NO: 3
Ipomoea batatas   AACAAGTCTG  CGGTAGTTTA  AAACTGAAT  TGCCACAATA  TGCGGAAGTG  GCCGCCTTTG SEQ ID NO: 9
174F
81F                                                                             --CGCCTTTG SEQ ID NO: 5
141F
174R
108R
81R
141R 1141
108F              CTCAATTTGG  CTCAGA----                                                   SEQ ID NO: 3
Ipomoea batatas   CTCAATTTGG  CTCAGACCTT  GATGCAGCGA  CTCAGGCATT  ACTCAATAGA  GGTGCAAGGC SEQ ID NO: 9
174F
81F               CTCAATTTGG  CTCAGA----                                                   SEQ ID NO: 5
141F
174R
108R
81R                                                                        -A  GGTGCAAGGC SEQ ID NO: 12
141R 1201
108F
Ipomoea batatas   TGACAGAAGT  ACTGAAACAA  CCACAATATG  CACCACTGCC  AATTGAAAAA  CAAATTCTAG SEQ ID NO: 9
174F
81F
141F
174R
108R                              ---ACAA  CCACAATATG  CACCACTGCC                          SEQ ID NO: 11
81R               TGACAGAAGT  ACT------                                                   SEQ ID NO: 12
141R 1261
108F
Ipomoea batatas   TAATTTATGC  AGCTGTCAAT  GGATTCTGTG  ATC  SEQ ID NO: 9
174F
81F
141F
174R
108R
81R
141R
```

METHODS AND COMPOSITIONS TO EVALUATE AND DETERMINE INACTIVATION OF HAZARDOUS BIOLOGICAL MATERIAL

CROSS REFERENCE TO RELATED APPLICATION

This application is a National Phase Application filed under 35 U.S.C. § 371 as a national stage of PCT/US2014/054749, filed on Sep. 9, 2014, and claims priority to U.S. Provisional Patent Application Ser. No. 61/876,425 filed Sep. 11, 2013 and U.S. Provisional Patent Application Ser. No. 61/969,465 filed Mar. 24, 2014, each of which are incorporated herein by reference in their entirety.

BACKGROUND OF THE INVENTION

Field of the Invention

This invention relates to assays to evaluate and/or determine the inactivation of biological material in/on a sample by quantifying the level of integrity, or alternatively, the degradation of, DNA and the materials necessary to perform the assays. The sample can be a food product (e.g., fruits, vegetables, meat from animals, or eggs) while the item can be any object (e.g., medical equipment, especially reusable medical equipment) for which one needs to determine that the amount of inactivation of specific hazardous biological material on the object or in a sample is at or below a pre-determined amount. Non-limiting examples of hazardous biological material are toxins, viruses, parasites, fungi, bacteria, spores (bacterial, fungal or parasitical) and cancer cells. This invention further relates to the tools used in the assays. One assay uses quantitative PCR and polynucleotide primers to assay the fragmentation of mitochondrial DNA found intrinsically in the food matrix. Another assay examines the size and fragmentation of total DNA present in the food matrix using any device which measures DNA fragment size globally. A third assay involves use of an extrinsic source of mitochondrial DNA added to the processing run in a recoverable container.

The official copy of the sequence listing is submitted electronically via EFS-Web as an ASCII formatted sequence listing with a file name "Perez-Diaz_seq_ST25_8-25-14.txt", created on Oct. 25, 2014, and having a size of 6 kilobytes and is filed concurrently with the specification. The sequence listing contained in this ASCII formatted document is part of the specification and is herein incorporated by reference in its entirety.

Description of the Prior Art

In order to render food products (both processed and fresh food products) safe and to prevent them from spoiling under the usual conditions of storage, some form of commercial sterilization is required. Control of food-borne bacterial pathogens such as *Salmonella* spp., *Shigella* spp., pathogenic *Escherichia coli*, *Campylobacter* spp., and *Yersinia* spp. has traditionally been achieved using heat treatments such as pasteurization or pressure sterilization. Heat treatments higher than pasteurization are used to provide *Clostridium botulinum* safety in low-acid canned foods and canned cured meats. Low-acid products have a pH of approximately 4.6 and above and include most meat and marine products, corn, peas, lima beans, asparagus and spinach. More recently, inhibition of surviving *Clostridium botulinum* spores has been achieved by treating food with $NaNO_2$ and/or potassium sorbate. Failure to adequately inactivate *Clostridium botulinum* spores can result in the production of neurotoxins by the bacteria. Of course, failure to destroy other disease causing bacteria (e.g., *Salmonella* spp., *Shigella* spp., pathogenic *E. coli*, *Campylobacter* spp., and *Yersinia* spp.) in food products can result in food poisoning and severe disease after ingesting the contaminated food products. In addition, butchered meats and raw eggs can become contaminated with pathogenic bacteria during the handling and/or processing of the meats and eggs. It is vital to reduce or eliminate the bacteria on the surface of these items so that the workers and people that consume the food are not sickened by the bacteria.

Food spoilage and food poisoning from contamination of food by bacteria is a major problem throughout the world, including developed countries such as the United States, Canada, Japan, U.K., France, Germany, and Russia. In the U.S. alone, illness from food-borne bacteria costs several billion dollars annually in morbidity and mortality. Gram-positive and Gram-negative food-borne bacteria account for many of the pathogens causing food poisoning.

Traditional safety guidelines have traditionally used destruction of bacterial surrogates as indicators of processing safety and efficacy. Culturing samples of food or items for viability of bacteria and/or spores is a current method for assaying the destruction of bacterial surrogates. Two bacterial surrogates are *Geobacillus stearothermophilus* and *Bacillus subtilis* spores which are placed in or on samples prior to inactivation and which are cultured after treatment to determine if the bacteria and/or the bacterial spores have been inactivated. Problems with the culture approach include tracking and recovering indicator spores and/or bacteria, excessive time required to culture (48 hours or more), and molecular methods unable to differentiate between live and dead surrogates. Other devices and methods have been created to assay for live or killed bacteria and bacterial spores in food and devices using various culturing conditions (e.g., US Pub. 2007-0249040; U.S. Pat. Nos. 5,486,459; 5,830,683; 5,989,852; and WO 1995/008639), yet these methods and devices lack the ability to timely and accurately determine the amount of reduction of viable hazardous biological materials in or on a food or item.

To overcome the limitation of the long incubation times required for the proliferation of microbes and/or bacterial spores, time and temperature integrator (TTI) technologies have been developed. An example of such technologies is the application of enzymes derived from microbes that can naturally tolerate high temperatures and need such high temperatures to proliferate. For example, α-amylase from *Bacillus licheniformis* (Cordt, et al., *J. Chem. Tech. and Biotech.* 59:193-199 (1994)), lipase (U.S. Pat. No. 4,284,719), and β-glucosidase (Adams and Langley, *Food Chemistry*, 62:65-68 (1998)) have been used as TTIs. These enzymes can be produced in high concentrations using molecular biology techniques. The pure enzyme is then encapsulated in plastic tubing with 1 mm diameter, and the ends are sealed by melting. The encapsulated enzyme can be incorporated in a food matrix and recovered after thermal treatment (e.g., pasteurization) of the food matrix is applied. The activity of the post-thermal treated, heat resistant enzyme is determined and correlated with the effectiveness of the heating step. This rapid method allows for evaluation of thermal treatments uniformity and effectiveness. However, production of enzymatic TTI is complex. Also, TTI's enzymatic activity is difficult to maintain during long storage periods and may vary within multiple production batches.

Alternative approaches to culturing bacteria and enzymatic TTI, include assays for bacterial DNA or mRNA in samples of food using PCR and PCR-related techniques. See, e.g., U.S. Patent App. Pub. 2010-0167956 in which polynucleotide probes specific for E. coli are placed on a chip for assaying for the presence of E. coli; and U.S. Patent App. Pub. 2012-0288864 in which S. enterica, a food-borne pathogen, is detected by PCR using primers specific for an S. enterica gene.

The effect of high temperature on DNA degradation is well described. Above 100° C. denaturation, depurination, deamination and loss of secondary structure occurs (Gryson, N., Anal. Bioanal. Chem. 396:2003-2022 (2010)). Although autoclaving a foodstuff at 121° C. for fifteen minutes does not destroy all DNA available for PCR (Lipp, et al., J. AOAC Int. 82(4):923-928 (1999)), recovery of reduced DNA concentrations via quantitative PCR (qPCR) from cornmeal and water cooked for sixty minutes at 100° C. have been reported (Murray, et al., J. of Agric. & Food Chem. 55:2231-2239 (2007)). Increased Ct (threshold cycles) values occurred in DNA from heat-treated corn grits and corn flour when compared to untreated corn and resulted in distortions of qPCR assays for detection of genetically modified organisms (GMO) (Moreano, et al., J. of Agric. & Food Chem. 53:9971-9979 (2005)).

However, these prior art methods for detecting bacteria via PCR are unable to determine if the bacteria or their spores are still viable or not because PCR often is able to detect a certain fragment of DNA from the bacteria or spores, despite their death or inactivation. In a study by Stam (Doctoral Thesis, NCSU Food Science; Raleigh, N.C. (2008), available at http://www.lib.ncsu.edu/resolver/1840.16/3192), Clostridium sporogenes spores were heat-treated to 121° C. in two minutes intervals for eighteen minutes, and bacterial DNA degradation over time was determined. It was noted that heat-treating the spores for only two minutes resulted in the absence of DNA bands using agarose gel electrophoresis. However, the autoclaved spore DNA was still detectable by qPCR, having a reduced Ct value of 35 compared to a Ct of 12 for viable spores (Stam (2008)). Therefore, bacterial or spore DNA is degraded but still detectable by qPCR, when using thermal processing techniques such as heat or microwave suitable for preserving vegetables and fruits. Obviously, the repercussions of being wrong about viability of biological material in or on food or other items are serious and could result in serious morbidity and possible mortality in humans. It can also lead to false positives, which have a negative financial impact on the food industry. Also, excessively heating food matrices to destroy bacterial or bacterial spores DNA is also problematic because the quality of the texture, flavor and appearance of the finish good is reduced.

In addition to food substances, many other items need to be rendered sterile or have a reduction in the viability of biological material on the items prior to usage. For example, reusable medical and dental devices (such as, but not limited to, endoscopes, catheters, sponges, clamps, scalpels, drills, and suction tubes) need to be cleaned (biological material inactivated) after being used on one subject, prior to use on another subject. Biological material present on robust medical equipment is often inactivated by subjecting the contaminated equipment to high temperatures and pressure via a steam autoclave. While such inactivation methods are very effective for more durable medical instruments, advanced medical instruments formed of rubber and plastic components with adhesives are delicate and wholly unsuited to the high temperatures and pressures associated with a conventional steam autoclave. Thus, some steam autoclaves have been modified to operate under low pressure cycling programs to increase the rate of steam penetration into the medical devices or associated packages of medical devices undergoing cleaning. However, highly complex instruments which are often formed and assembled with very precise dimensions, close assembly tolerances, and sensitive optical components, such as endoscopes, may be destroyed or have their useful lives severely curtailed by harsh inactivation methods employing high temperatures and high or low pressures. Endoscopes, in particular, present problems in that such devices typically have numerous exterior crevices and interior lumens which can harbor microbes and thus be difficult to clean using ordinary techniques. The employment of a fast-acting yet gentle inactivation method is desirable for reprocessing sensitive instruments. Other medical or dental instruments which comprise lumens are also in need of methods of cleaning which employ an effective reprocessing system which will not harm sensitive components and materials. Further, the need exists for a reprocessing system having a shorter reprocessing cycle time. Regardless of how these devices are cleaned, failure to inactivate a substantial proportion of the biological material that may be present on the item after usage could result in the dangerous illness in the next subject on which the item is used.

The Food Safety Modernization Act (FSMA) mandates that companies document risk-based preventive controls for all pre-requisite programs as part of their Food Safety program. The Food and Drug Administration proposed guidelines under FSMA include the application of prevention standards to sanitation and environmental controls and monitoring. For example, one of the modifications under consideration involves sterilization of food packaging containers prior to filling the containers. Glass jars used for packaging of finished acidified and acid foods for the retail market are currently rinse with hot water, filled with the product, and subjected to a validated pasteurization step, often considered as a critical control point to render the finished food safe for consumption. New guidelines would require such containers to be subjected to a sterilization treatment prior to filling. The sterilization step for glass containers could be applied as a pasteurization, ultraviolet light, high pressure, or radiation treatment. The effectiveness of such treatments to eradicate pathogens of public health significance would have to be demonstrated after the treatments are applied.

As such, there remains a need for one or more assays that can evaluate and/or determine the amount of inactivation of biological material on/in food and/or an object in a timely and accurate manner. There is also a need for assays that can evaluate inactivation protocols and for evaluating deviations in processing to reduce the amount of viable biological material in/on items. The assays described herein use quantitative PCR. PCR and real-time PCR are well-known laboratory techniques and are accepted by AOAC International for clinical detection assays, including assays to detect BRCA1 and BRCA2 mutations.

Mitochondrial DNA (mtDNA) is used as identifiers in many scientific disciplines. They have been adopted for barcoding almost all groups of higher animals (http://www.barcoding.si.edu/). MtDNA is also used in human typing for forensic analysis (Hopwood, et al., Int. J. Legal Med. 108(5):237-243 (1996); Andreasson, et al., Biotechniques 33(2):402-411 (2002); Budowle, et al., Annu. Rev. Genomics Hum. Genet. 4:119-141 (2003)) using tissues such as bones, teeth, and hair shafts for DNA extraction. MtDNA primers or probes have been developed for source tracking fecal contaminates in wastewater influents and effluents using multiplex qPCR (Caldwell, et al., Environ. Sci. & Technol., 41:3277-83 (2007); Caldwell and Levine, *J. Microbiol. Methods* 77:17-22 (2009); Caldwell, et al., "Mitochondrial DNA as source tracking markers of fecal contamination", In *Microbial Source Tracking: Methods, Applications, and Case Studies*, eds. Harwood, Hagedorn and Blanch (Springer Science and Business Media, NY) 229-250 (2011)). In the food industry, PCR-based mtDNA analyses are used in the authentication of food, and to trace contamination of other animals in the food products (Meyer and Candrian, *Lebensm.—Wiss. u.—Technol.* 29:1-9 (1996); Lahiff, et al., *Mol. Cell Probes* 15(1):27-35 (2001); Zhang, et al., *Food Control* 18:1149-1158 (2007); Fujimura, et al., *Biosci. Biotechnol. Biochem.* 72:909-913 (2008)). The development of those molecular tools improved the monitoring of food quality by preventing fraudulent description of food content, and identifying adulterants.

SUMMARY OF THE INVENTION

It is an object of this invention to have a synthetic polynucleotide which has a nucleic acid sequence that is a consensus sequence to a portion of a gene that is highly conserved in plants and/or animals. It is a further object of this invention that this synthetic polynucleotide is between approximately 80 bp and approximately 250 bp long. It is a further object of this invention that this synthetic polynucleotide is between approximately 100 bp and approximately 200 bp long. It is a further object of this invention that this synthetic polynucleotide is between approximately 125 bp and approximately 175 bp long. It is a further object of this invention that the highly conserved gene be a mitochondrial gene. It is a further object of this invention that the mitochondrial gene be atp1. It is a further object of this invention that the sequence of this synthetic polynucleotide be at least 95% identical to the sequence of a portion of atp1. It is another object of this invention that this synthetic polynucleotide has the sequence selected from the group consisting of SEQ ID NO: 14, 15, 16, and 17, or a sequence that is the reverse complement thereof.

It is an object of this invention to have a synthesized polynucleotide which a consensus sequence to a portion of a gene that is highly conserved in plants and/or animals. It is a further object of this invention that the highly conserved gene be a mitochondrial gene. It is a further object of this invention that the mitochondrial gene be atp1. It is a further object of this invention that the sequence of this synthetic polynucleotide be at least 95% identical to the sequence of a portion of atp1. It is another object of this invention that the polynucleotide has a sequence selected from the group consisting of SEQ ID NO: 1, 2, 3, 4, 5, 6, 7, and 8.

It is an object of this invention to have a composition useful for determining the integrity of a mitochondrial DNA gene, the composition containing a probe, a quencher dye, and a fluorescent dye. It is another object of this invention that the quencher dye and fluorescent dye are linked to the probe. It is a further object of this invention that the probe has a nucleotide sequence of between approximately any 15 contiguous bases and approximately any 45 contiguous bases selected from the sequences in SEQ ID NO: 14, 15, 16, and 17, and the reverse complement thereof.

It is an object of this invention to have a kit or composition that is useful for determining the integrity of a mitochondrial DNA gene, the kit or composition containing a first polynucleotide and a second polynucleotide and, optionally, instructions for using the first polynucleotide and second polynucleotide, and optionally, a DNA polymerase. It is another object of this invention that the first polynucleotide and second polynucleotide have sequences which are at least 95% identical to a portion of a mitochondrial DNA gene. It is another object of this invention that the sequences of the first polynucleotide and second polynucleotide are at least 95% identical to a portion of the atp1. It is a further object of this invention that the first polynucleotide and the second polynucleotide have the sequences as follows: the first polynucleotide has SEQ ID NO: 1 and the second polynucleotide has SEQ ID NO: 2; the first polynucleotide has SEQ ID NO: 3 and the second polynucleotide has SEQ ID NO: 4; the first polynucleotide has SEQ ID NO: 5 and the second polynucleotide has SEQ ID NO: 6; and the first polynucleotide has SEQ ID NO: 7 and the second polynucleotide has SEQ ID NO: 8. It is a further object of this invention that the kit or composition optionally contain a fluorescent composition that can be either an intercalating dye or a composition of a fluorescent dye, a quencher dye and a probe such that the fluorescent dye and quencher dye are linked to the probe. It is another object of this invention that the probe have a sequence of between approximately fifteen contiguous bases and approximately forty-five contiguous bases of SEQ ID NO: 14 or the reverse complement thereof when the first polynucleotide has SEQ ID NO: 1 and the second polynucleotide has SEQ ID NO: 2; or a sequence of between approximately fifteen contiguous bases and approximately forty-five contiguous bases SEQ ID NO: 15 or the reverse complement thereof when the first polynucleotide has SEQ ID NO: 3 and the second polynucleotide has SEQ ID NO: 4; or a sequence of between approximately fifteen contiguous bases and approximately forty-five contiguous bases of SEQ ID NO: 16 or the reverse complement thereof when the first polynucleotide has SEQ ID NO: 5 and the second polynucleotide has SEQ ID NO: 6; or a sequence of between approximately fifteen contiguous bases and approximately forty-five contiguous bases of SEQ ID NO: 17 or the reverse complement thereof when the first polynucleotide has SEQ ID NO: 7 and the second polynucleotide has SEQ ID NO: 8.

It is an object of this invention to have a method for determining the amount of inactivation of hazardous biological material in a food matrix, the method having the steps of exposing the food matrix's intrinsic DNA to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value of food material intrinsic DNA that is equivalent to the desired amount of inactivation of said hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is another object of the invention that the food matrix is plant material, animal material, or a combination thereof. It is another object of this invention that the fluorescent composition can be an intercalating dye or a composition of a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof.

It is an object of this invention to have a method for determining the amount of inactivation of hazardous biological material in a food matrix, the method having the steps of exposing the food matrix's intrinsic DNA to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value of food material intrinsic DNA that is equivalent to the desired amount of inactivation of said hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is another object of this invention that the first polynucleotide has a sequence of between approximately 15 contiguous bases and approximately 45 contiguous bases of SEQ ID NO: 9, and the second polynucleotide has a sequence of between approximately 15 contiguous bases and approximately 45 contiguous bases of the reverse complement of SEQ ID NO: 9, and the amplicon generated is between approximately 80 bp and 250 bp long, is between approximately 100 bp and approximately 200 bp long, or is between approximately 125 bp and approximately 175 bp long. It is another object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 9 or the reverse complement thereof. It is another object of this invention to have the step of isolating the intrinsic DNA from the food matrix prior to exposing the intrinsic DNA to the first polynucleotide and second polynucleotide. It is another object of the invention that the food matrix is plant material, animal material, or a combination thereof.

It is an object of this invention to have a method for determining the amount of inactivation of hazardous biological material in a food matrix, the method having the steps of exposing the food matrix's intrinsic DNA to a first polynucleotide, a second polynucleotide, and optionally to a fluorescent composition; amplifying the intrinsic DNA using a DNA amplification method to produce an amplicon; determining the threshold cycle of the amplified intrinsic DNA; and comparing the obtained threshold cycle value to a known threshold cycle value of food material intrinsic DNA that is equivalent to the desired amount of inactivation of said hazardous biological material. It is a further object of this invention that the DNA amplification method use DNA polymerase to generate an amplicon that has the sequence of SEQ ID NO: 14. It is another object of this invention that the first polynucleotide has the sequence of SEQ ID NO: 1, and the second polynucleotide has a sequence of SEQ ID NO: 2 or the reverse complement thereof. It is another object of this invention to have the step of isolating the intrinsic DNA from the food matrix prior to exposing the intrinsic DNA to the first polynucleotide and second polynucleotide. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 14 or the reverse complement thereof. It is another object of the invention that the food matrix is plant material, animal material, or a combination thereof.

It is an object of this invention to have a method for determining the amount of inactivation of hazardous biological material in a food matrix, the method having the steps of exposing the food matrix's intrinsic DNA to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value of food material intrinsic DNA that is equivalent to the desired amount of inactivation of said hazardous biological material. It is a further object of this invention that the DNA amplification method use DNA polymerase to generate an amplicon that has the sequence of SEQ ID NO: 15. It is another object of this invention that the first polynucleotide has the sequence of SEQ ID NO: 3, and the second polynucleotide has a sequence of SEQ ID NO: 4 or the reverse complement thereof. It is another object of this invention to have the step of isolating the intrinsic DNA from the food matrix prior to exposing the intrinsic DNA to the first polynucleotide and second polynucleotide. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 15 or the reverse complement thereof. It is another object of the invention that the food matrix is plant material, animal material, or a combination thereof.

It is an object of this invention to have a method for determining the amount of inactivation of hazardous biological material in a food matrix, the method having the steps of exposing the food matrix's intrinsic DNA to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value of food material intrinsic DNA that is equivalent to the desired amount of inactivation of said hazardous biological material. It is a further object of this invention that the DNA amplification method use DNA polymerase to generate an amplicon that has the sequence of SEQ ID NO: 16. It is another object of this invention that the first polynucleotide has the sequence of SEQ ID NO: 5, and the second polynucleotide has a sequence of SEQ ID NO: 6 or the reverse complement thereof. It is another object of this invention to have the step of isolating the intrinsic DNA from the food matrix prior to exposing the intrinsic DNA to the first polynucleotide and second polynucleotide. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 16 or the reverse complement thereof. It is another object of the invention that the food matrix is plant material, animal material, or a combination thereof.

It is an object of this invention to have a method for determining the amount of inactivation of hazardous biological material in a food matrix, the method having the steps of exposing the food matrix's intrinsic DNA to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value of food material intrinsic DNA that is equivalent to the desired amount of inactivation of said hazardous biological material. It is a further object of this invention that the DNA amplification method use DNA polymerase to generate an amplicon that has the sequence of SEQ ID NO: 17. It is another object of this invention that the first polynucleotide has the sequence of SEQ ID NO: 7, and the second polynucleotide has a sequence of SEQ ID NO: 8 or the reverse complement thereof. It is another object of this invention to have the step of isolating the intrinsic DNA from the food matrix prior to exposing the intrinsic DNA to the first polynucleotide and second polynucleotide. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 17 or the reverse complement thereof. It is another object of the invention that the food matrix is plant material, animal material, or a combination thereof.

It is an object of this invention to have a method for determining the efficacy of a protocol to inactivate hazardous biological material in a food matrix having the steps of, optionally processing a food matrix sample according to the inactivation protocol; exposing the intrinsic DNA of the food matrix processed according to the inactivation protocol to a first polynucleotide, a second polynucleotide, and optionally a fluorescent composition; amplifying the intrinsic DNA using an amplification process to produce an amplicon; determining the threshold cycle of the amplified intrinsic DNA; and comparing the obtained threshold cycle value to a known threshold cycle value for the intrinsic DNA of the food material that has been processed according to a second inactivation method known to achieve the desired amount of inactivation of the hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is another object of the invention that the food matrix is plant material, animal material, or a combination thereof. It is another object of this invention that the first polynucleotide and second polynucleotide bind to mtDNA. It is another object of this invention that the first polynucleotide and second polynucleotide bind to atp1. It is another object of this invention to optionally have the step of isolating the intrinsic DNA from the processed food matrix prior to exposing the intrinsic DNA to the first polynucleotide and second polynucleotide. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof.

It is an object of this invention to have a method for determining the efficacy of a protocol to inactivate hazardous biological material in a food matrix having the steps of, optionally processing a food matrix sample according to the inactivation protocol; exposing the intrinsic DNA of the food matrix processed according to the inactivation protocol to a first polynucleotide, a second polynucleotide, and optionally a fluorescent composition; amplifying the intrinsic DNA using an amplification process to produce an amplicon; determining the threshold cycle of the amplified intrinsic DNA; and comparing the obtained threshold cycle value to a known threshold cycle value for the intrinsic DNA of the food material that has been processed according to a second inactivation method known to achieve the desired amount of inactivation of the hazardous biological material. It is another object of this invention that the first polynucleotide has a sequence of between approximately 15 contiguous bases and approximately 45 contiguous bases of SEQ ID NO: 9, and the second polynucleotide has a sequence of between approximately 15 contiguous bases and approximately 45 contiguous bases of the reverse complement of SEQ ID NO: 9, and the amplicon generated is between approximately 80 bp and 250 bp long, is between approximately 100 bp and approximately 200 bp long, or is between approximately 125 bp and approximately 175 bp long. It is a further object of this invention that the DNA amplification method use DNA polymerase to generate the amplicon. It is another object of this invention to optionally have the step of isolating the intrinsic DNA from the processed food matrix prior to exposing the intrinsic DNA to the first polynucleotide and second polynucleotide. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof. It is another object of the invention that the food matrix is plant material, animal material, or a combination thereof.

It is an object of this invention to have a method for determining the efficacy of a protocol to inactivate hazardous biological material in a food matrix having the steps of, optionally processing a food matrix sample according to the inactivation protocol; optionally isolating the intrinsic DNA of the processed food matrix; exposing the intrinsic DNA of the food matrix processed according to the inactivation protocol to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value for the intrinsic DNA of the food material that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 14. It is another object of this invention that the first polynucleotide has the sequence of SEQ ID NO: 1, and the second polynucleotide has a sequence of SEQ ID NO: 2 or the reverse complement thereof. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 14 or the reverse complement thereof. It is another object of the invention that the food matrix is plant material, animal material, or a combination thereof.

It is an object of this invention to have a method for determining the efficacy of a protocol to inactivate hazardous biological material in a food matrix having the steps of, optionally processing a food matrix sample according to the inactivation protocol; optionally isolating the intrinsic DNA of the processed food matrix; exposing the intrinsic DNA of the food matrix processed according to the inactivation protocol to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value for the intrinsic DNA of the food material that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 15. It is another object of this invention that the first polynucleotide has the sequence of SEQ ID NO: 3, and the second polynucleotide has a sequence of SEQ ID NO: 4 or the reverse complement thereof. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 15 or the reverse complement thereof. It is another object of the invention that the food matrix is plant material, animal material, or a combination thereof.

It is an object of this invention to have a method for determining the efficacy of a protocol to inactivate hazardous biological material in a food matrix having the steps of, optionally processing a food matrix sample according to the inactivation protocol; optionally isolating the intrinsic DNA of the processed food matrix; exposing the intrinsic DNA of the food matrix processed according to the inactivation protocol to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value for the intrinsic DNA of the food material that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 16. It is another object of this invention that the first polynucleotide has the sequence of SEQ ID NO: 5, and the second polynucleotide has a sequence of SEQ ID NO: 6 or the reverse complement thereof. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 16 or the reverse complement thereof. It is another object of the invention that the food matrix is plant material, animal material, or a combination thereof.

It is an object of this invention to have a method for determining the efficacy of a protocol to inactivate hazardous biological material in a food matrix having the steps of, optionally processing a food matrix sample according to the inactivation protocol; optionally isolating the intrinsic DNA of the processed food matrix; exposing the intrinsic DNA of the food matrix processed according to the inactivation protocol to a first polynucleotide, a second polynucleotide, and optionally a fluorescent composition; amplifying the intrinsic DNA using a DNA amplification method to produce an amplicon; determining the threshold cycle of the amplified intrinsic DNA; and comparing the obtained threshold cycle value to a known threshold cycle value for the intrinsic DNA of the food material that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 17. It is another object of this invention that the first polynucleotide has the sequence of SEQ ID NO: 7, and the second polynucleotide has a sequence of SEQ ID NO: 8 or the reverse complement thereof. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 17 or the reverse complement thereof. It is another object of the invention that the food matrix is plant material, animal material, or a combination thereof.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, to a second polynucleotide, and optionally a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof. It is a further object of this invention that the item be a food matrix, a container, equipment, or a medical device.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, to a second polynucleotide, and optionally to a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is another object of this invention that the first polynucleotide has a sequence of between approximately 15 contiguous bases and approximately 45 contiguous bases of any mtDNA gene, and the second polynucleotide has a sequence of between approximately 15 contiguous bases and approximately 45 contiguous bases of the reverse complement of the same mtDNA gene, and the amplicon generated is between approximately 80 bp and 250 bp long, is between approximately 100 bp and approximately 200 bp long, or is between approximately 125 bp and approximately 175 bp long. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof. It is a further object of this invention that the item be a food matrix, a container, equipment, or a medical device.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, a second polynucleotide, and optionally a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is another object of this invention that the first polynucleotide has a sequence of between approximately 15 contiguous bases and approximately 45 contiguous bases of SEQ ID NO: 9, and the second polynucleotide has a sequence of between approximately 15 contiguous bases and approximately 45 contiguous bases of the reverse complement of SEQ ID NO: 9, and the amplicon generated is between approximately 80 bp and 250 bp long, is between approximately 100 bp and approximately 200 bp long, or is between approximately 125 bp and approximately 175 bp long. It is a further object of this invention that the fluorescent composition be an intercalating dye or a composition containing a fluorescent dye, a quencher dye and a probe such that the fluorescent dye and quencher dye are linked to the probe and such that the probe has a sequence of between approxi-mately 15 contiguous bases and approximately 45 contiguous bases of the amplicon or the reverse complement thereof. It is a further object of this invention that the item be a food matrix, a container, equipment, or a medical device.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, a second polynucleotide, and optionally a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 14; that the first polynucleotide has the sequence of SEQ ID NO: 1, and the second polynucleotide has the sequence of SEQ ID NO: 2. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 14 or the reverse complement thereof. It is a further object of this invention that the item be a food matrix, a container, equipment, or a medical device.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, a second polynucleotide, and optionally a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 15; that the first polynucleotide has the sequence of SEQ ID NO: 3, and the second polynucleotide has the sequence of SEQ ID NO: 4. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 15 or the reverse complement thereof. It is a further object of this invention that the item be a food matrix, a container, equipment, or a medical device.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, a second polynucleotide, and optionally a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 16; that the first polynucleotide has the sequence of SEQ ID NO: 5, and the second polynucleotide has the sequence of SEQ ID NO: 6. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 16 or the reverse complement thereof. It is a further object of this invention that the item be a food matrix, a container, equipment, or a medical device.

It is an object of this invention to have a method for assessing the efficacy of a protocol for inactivation of hazardous material in or on an item, the method having the steps of optionally processing a sample of extrinsic DNA according to the protocol; optionally isolating the processed extrinsic DNA; exposing the extrinsic DNA to a first polynucleotide, a second polynucleotide, and optionally a fluorescent composition; amplifying the extrinsic DNA using a DNA amplification method to produce an amplicon; determining the threshold cycle of the extrinsic DNA; and comparing the obtained threshold cycle value to a known threshold cycle value for extrinsic DNA that has been processed according to a second inactivation method known to achieve the desired amount of inactivation of the hazardous biological material. It is a further object of this invention that the DNA amplification method use DNA polymerase to generate an amplicon that has the sequence of SEQ ID NO: 17; that the first polynucleotide has the sequence of SEQ ID NO: 7, and the second polynucleotide has the sequence of SEQ ID NO: 8. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 17 or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; exposing the intrinsic DNA or extrinsic DNA to a first polynucleotide, a second polynucleotide, and optionally a fluorescent composition; amplifying the intrinsic DNA or extrinsic DNA using a DNA amplification method to produce an amplicon; determining the threshold cycle of the intrinsic DNA or extrinsic DNA; and comparing the obtained threshold cycle value to a known threshold cycle value for intrinsic DNA or extrinsic DNA that is equivalent to the desired amount of inactivation of the hazardous biological material. It is a further object of this invention that the DNA amplification method use DNA polymerase to generate an amplicon that is between approximately 80 bp and approximately 250 bp long and that has the sequence of the first polynucleotide at the amplicon's 5' end and the sequence of the second polynucleotide at the amplicon's 3' end. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; exposing the intrinsic DNA or extrinsic DNA to a first polynucleotide, a second polynucleotide, and optionally a fluorescent composition; amplifying the intrinsic DNA or extrinsic DNA using a DNA amplification method to produce an amplicon; determining the threshold cycle of the intrinsic DNA or extrinsic DNA; and comparing the obtained threshold cycle value to a known threshold cycle value for intrinsic DNA or extrinsic DNA that is equivalent to the desired amount of inactivation of the hazardous biological material. It is a further object of this invention that the DNA amplification method use DNA polymerase to generate an amplicon that has the sequence of the first polynucleotide at the amplicon's 5' end and the sequence of the second polynucleotide at the amplicon's 3' end. It is another object of this invention that the first polynucleotide has a sequence of between approximately 15 contiguous bases and approximately 45 contiguous bases of SEQ ID NO: 9, and the second polynucleotide has a sequence of between approximately 15 contiguous bases and approximately 45 contiguous bases of the reverse complement of SEQ ID NO: 9, and the amplicon generated is between approximately 80 bp and 250 bp long, is between approximately 100 bp and approximately 200 bp long, or is between approximately 125 bp and approximately 175 bp long. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of the amplicon or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; exposing the intrinsic DNA or extrinsic DNA to a first polynucleotide, a second polynucleotide, and optionally a fluorescent composition; amplifying the intrinsic DNA or extrinsic DNA using a DNA amplification method to produce an amplicon; determining the threshold cycle of the intrinsic DNA or extrinsic DNA; and comparing the obtained threshold cycle value to a known threshold cycle value for intrinsic DNA or extrinsic DNA that is equivalent to the desired amount of inactivation of the hazardous biological material. It is a further object of this invention that the DNA amplification method use DNA polymerase to generate an amplicon that has the sequence of SEQ ID NO: 14; that the first polynucleotide has the sequence of SEQ ID NO: 1, and the second polynucleotide has the sequence of SEQ ID NO: 2. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 14 or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; exposing the intrinsic DNA or extrinsic DNA to a first polynucleotide, a second polynucleotide, and optionally a fluorescent composition; amplifying the intrinsic DNA or extrinsic DNA using a DNA amplification method to produce an amplicon; determining the threshold cycle of the intrinsic DNA or extrinsic DNA; and comparing the obtained threshold cycle value to a known threshold cycle value for intrinsic DNA or extrinsic DNA that is equivalent to the desired amount of inactivation of the hazardous biological material. It is a further object of this invention that the DNA amplification method use DNA polymerase to generate an amplicon that has the sequence of SEQ ID NO: 15; that the first polynucleotide has the sequence of SEQ ID NO: 3, and the second polynucleotide has the sequence of SEQ ID NO: 4. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 15 or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; exposing the intrinsic DNA or extrinsic DNA to a first polynucleotide, a second polynucleotide, and optionally a fluorescent composition; amplifying the intrinsic DNA or extrinsic DNA using a DNA amplification method to produce an amplicon; determining the threshold cycle of the intrinsic DNA or extrinsic DNA; and comparing the obtained threshold cycle value to a known threshold cycle value for intrinsic DNA or extrinsic DNA that is equivalent to the desired amount of inactivation of the hazardous biological material. It is a further object of this invention that the DNA amplification method use DNA polymerase to generate an amplicon that has the sequence of SEQ ID NO: 16; that the first polynucleotide has the sequence of SEQ ID NO: 5, and the second polynucleotide has the sequence of SEQ ID NO: 6. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 16 or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; exposing the intrinsic DNA or extrinsic DNA to a first polynucleotide, a second polynucleotide, and optionally a fluorescent composition; amplifying the intrinsic DNA or extrinsic DNA using a DNA amplification method to produce an amplicon; determining the threshold cycle of the intrinsic DNA or extrinsic DNA; and comparing the obtained threshold cycle value to a known threshold cycle value for intrinsic DNA or extrinsic DNA that is equivalent to the desired amount of inactivation of the hazardous biological material. It is a further object of this invention that the DNA amplification method use DNA polymerase to generate an amplicon that has the sequence of SEQ ID NO: 17; that the first polynucleotide has the sequence of SEQ ID NO: 7, and the second polynucleotide has the sequence of SEQ ID NO: 8. It is a further object of this invention that the fluorescent composition be an intercalating dye or a composition containing a fluorescent dye, a quencher dye and a probe such that the fluorescent dye and quencher dye are linked to the probe and such that the probe has a sequence of between approximately 15 contiguous bases and approximately 45 contiguous bases of SEQ ID NO: 17 or the reverse complement thereof. It is a further object of this invention that the item be a food matrix, a container, equipment, or a medical device.

It is an object of this invention to have a quality control method for determining the amount of inactivation of a hazardous material in or on an item, the method having the steps of optionally processing a sample containing either intrinsic DNA or extrinsic DNA according to the predetermined inactivation protocol; optionally isolating the processed intrinsic DNA or extrinsic DNA; running the intrinsic DNA or extrinsic DNA on a electrophoretic gel; determining the amount of DNA fragmentation for DNA sizes ranging from approximately 35 bp to approximately 10,380 bp; determining the DNA integrity number; and comparing the obtained DNA integrity number to a known DNA integrity number that is equivalent to the desired amount of inactivation of the hazardous biological material. It is a further object of this invention that the intrinsic DNA or extrinsic DNA be exposed to a fluorescent composition prior to or after running the intrinsic DNA or extrinsic DNA on the electrophoretic gel; such that the fluorescent composition is a fluorescent dye for imaging DNA. It is a further object of this invention that the item be a food matrix, a container, equipment, or a medical device.

BRIEF DESCRIPTION OF THE DRAWINGS

FIG. 9 shows the sequence of *I. batatas* atp1, the location of the primers used, and the sequences of the amplicons generated.

DETAILED DESCRIPTION OF THE INVENTION

Figure 1:
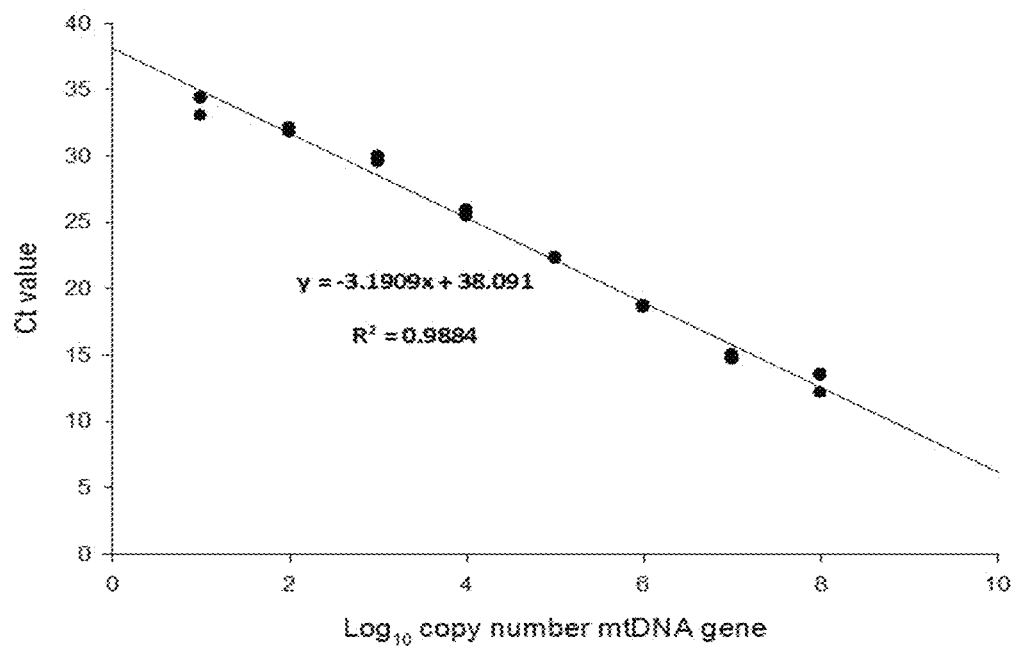
FIG. 1 illustrates the standard curve for qPCR for mtDNA copy number. The standard curve is also used to determine amplification efficiency of the protocol (106%), the limit of detection (10 copies) and the linear dynamic range (7 orders of magnitude).

This invention determines inactivation of biological material, primarily hazardous biological material such as in or on food or an item by quantifying the amount of degradation in a food matrix's intrinsic DNA or in extrinsic DNA added to food or an item. The amount of DNA degradation is correlated to inactivation of hazardous biological material such as disease causing pathogens, and/or widely accepted surrogates for bacterial pathogen's spores. More specifically, the quantified DNA degradation is a time/temperature indicator which is a surrogate for inactivation of hazardous biological material. When DNA degradation is at or after specified values, the inactivation of hazardous biological material in or on a food or item is assured. Because this process uses quantitative PCR, some commercially available reagents, and/or apparatuses, the assay is inexpensive and simple to use. Further, it provides an answer regarding inactivation of the hazardous biological material of interest significantly faster than prior art methods of culturing for biological material, and more accurately over prior art methods of using PCR to detect the presence of a pathogen's DNA. One method for determining DNA degradation is by performing quantitative PCR (qPCR) on specific genes contained in mitochondrial DNA (mtDNA) of the food matrix. A second method is to examine DNA integrity of a food matrix. A third method is to add mtDNA (extrinsic DNA) as an extrinsic source in a recoverable container. All three methods are used as time/temperature integrators. These assays serve as presumptive verification of processing efficacy. Using the tool box approach, these assays provide rapid results that a processor can use to evaluate the reduction in amount of viable hazardous biological material in or on an item (food, device, etc.) prior to shipping or using the item. These assays can also be used to evaluate deviations in normal processing of items and to evaluate the efficacy of new processing methods under consideration. These assays use mitochondrial DNA (mtDNA) fragmentation or DNA integrity to determine the degradation of DNA over the range of time, temperature, and other inactivation process' conditions such as, but not limited to, high pressure or ultraviolet light. MtDNA is a surrogate for the inactivation of hazardous biological material in or on the item being treated (food, device, etc.). DNA integrity, whether measuring intrinsic DNA integrity or extrinsic DNA integrity, is a surrogate for the inactivation of hazardous biological material in or on the item being treated (food, device, etc.). These methods can be used to determine if an appropriate reduction in viable hazardous biological material (bacteria, bacterial spores, viruses, fungi, parasites, cancer cells, etc.) occurs after the processing of the food matrix or device. An appropriate reduction in viable hazardous biological material could be a 5 log reduction of a particular pathogen or any other amount desired or required by regulations governing food safety or medical device safety. These methods can also be used as quality control for a particular inactivation process. These methods can also be used to assay the survival of hazardous biological material after processing.

Polymerase chain reaction (or PCR) is a technique to copy (or amplify) a small quantity of DNA. Using PCR, one can generate greater than 100,000,000 or even one billion copies of the desired DNA within a couple of hours. To amplify a segment of DNA using PCR, the sample is first heated so the DNA denatures (separates into two pieces of single-stranded DNA). Next, the sample is cooled to a temperature lower than the melting (or denaturing) temperature of the DNA but still substantially higher than room temperature. At this temperature primers bind specific, pre-determined sites. Taq polymerase (a DNA polymerase active at high temperatures) synthesizes two new strands of DNA, using the original strands as templates and primers that bind to the original strands of DNA as initiation points for DNA extension by Taq polymerase. Of course, sufficient amounts of free nucleic acids are added to the reaction mixture for use by Taq polymerase to generate the new DNA. This process results in the duplication of a section of the original DNA based on the binding location of the primers. Each new DNA segment (also referred to as an amplicon) contains one old and one new strand of DNA. The sample is heated again to denature the DNA again and allowed to cool so that Taq polymerase can generate new amplicons. The cycle of denaturing and synthesizing new DNA is repeated as many as thirty or forty times, leading to more than one billion amplicons. A thermocycler is a programmable apparatus that automates the temperature changes utilized in PCR, controlling DNA denaturation and synthesis. PCR can be completed in a few hours. Some early U.S. patents on PCR include U.S. Pat. Nos. 4,683,195; 4,683,202; and 4,800,159.

Quantitative PCR (qPCR), also called real-time PCR, involves monitoring DNA amplification during each cycle of PCR using fluorescent label. When the DNA is in the log linear phase of amplification, the amount of fluorescence increases above the background. The point at which the fluorescence becomes measurable is called the Threshold Cycle (Ct) or crossing point. By using multiple dilutions of a known amount of standard DNA, a standard curve can be generated of log concentration against Ct (see FIG. 1). The amount of DNA or cDNA in an unknown sample can then be calculated from its Ct value. Two types of fluorescent labels are used with qPCR. One label is an intercalating dye that incorporates into double-stranded DNA, such as, but not limited to, SYBR® Green. An intercalating dye is appropriate when a single amplicon is being studied. The second type of fluorescent label is a probe that binds specifically to the target DNA, such as TaqMan® probes, Molecular Beacons™, or Scorpion primers. The probe is labeled with a fluorescent dye (such as, but not limited to Texas Red®, FAM, TET, HEX, TAMRA, JOE, and ROX) and a quencher (such as, but not limited to Dabcyl and Dabsyl). The oligonucleotide itself has no significant fluorescence, but fluoresces either when annealed to the template (as in Molecular Beacons™) or when the dye is clipped from the oligonucleotide during extension (as in TaqMan® probes). Multiplex PCR is possible by using dyes with different fluorescent emissions for each probe. The fluorescent compositions described herein are simply examples of compositions for imaging, identifying, and/or quantifying DNA. Instead of the fluorescent compositions described herein, one can label DNA with compositions that are known in the art (some of which are described infra) or that are developed in the future. These labels can be used to image, identify, and/or quantify DNA using similar methods as described herein. The fluorescent compositions are simply one well-known and well-accepted compositions for imaging, identifying, and/or quantifying DNA for the methods described herein.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs) and locked nucleic acids (RNA monomers with a modified backbone). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

The term "label" as used herein, refers to a composition detectable by spectroscopic, photochemical, biochemical, immunochemical, or chemical means. Exemplary labels include $^{32}P$, fluorescent dyes, electron-dense reagents, enzymes (e.g., as commonly used in an ELISA), biotin, digoxigenin, or haptens and proteins for which antisera or monoclonal antibodies are available.

As used herein a nucleic acid "probe", oligonucleotide "probe", or simply a "probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "probe" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically a DNA oligonucleotide of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of a promoter complex sequence will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence. When discussing primer pairs, one provides the sequence of both the forward and reverse primers in the 5' to 3' direction and is the sequence of the positive strand of DNA. However, when performing PCR, the sequence of the reverse primer actually used is the reverse complement of the sequence of the reverse primer. Thus for 174R primer, the actual sequence used is in SEQ ID NO: 10; for 108R primer, the actual sequence uses is in SEQ ID NO: 11; for 81R primer, the actual sequence used is in SEQ ID NO: 12; and for 141R primer, the actual sequence used is in SEQ ID NO: 13.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons).

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a nucleic acid of interest. Hybridization of the first and second nucleic acids is conducted under standard stringent conditions, e.g., high temperature and/or low salt content, which tend to disfavor hybridization of dissimilar nucleotide sequences.

The terms "identical" or percent "identity", in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984. *Nuc. Acids Res.* 12:387-395.

The phrase "selectively hybridizes to" or "specifically hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Intrinsic DNA means nucleic acids (DNA or RNA) that are present naturally in a sample, including nucleic acids from hazardous biological material present in the sample. For example, intrinsic DNA for a food matrix is the DNA and RNA in the cells of the plant or animal ingredients in the food matrix. Intrinsic DNA includes mitochondrial DNA (mtDNA), but is not limited to mtDNA.

Extrinsic DNA means any nucleic acids (DNA or RNA) added to a system for inactivating hazardous biological material. Usually, the extrinsic DNA is double-stranded polynucleotide which can range from between approximately 80 bp to approximately 250 bp long. Extrinsic DNA does not need to be from any particular gene or non-coding region. However, one must have primers, and optionally a labeled probe, which can be used while performing qPCR on the extrinsic DNA. The extrinsic DNA is used when one does not have or does not want to perform qPCR on intrinsic DNA to determine the efficacy of an inactivation process. For example, when determining if a certain process is sufficient robust to destroy hazardous biological material present on an item (e.g., a jar or medical device), one subjects a test sample of extrinsic DNA in a low pH solution or high pH solution to the inactivation process. An item, optionally, may or may not be subjected to the inactivation process with the extrinsic DNA. Then one performs the qPCR assays described herein on the extrinsic DNA to determine the amount of nucleic acid degradation and correlate that degradation to the destruction/inactivation of hazardous biological material on/in the item.

DNA degradation, RNA degradation, nucleic acid degradation are the breaking of the chemical bonds with the nucleic acids so that the organism containing those degraded nucleic acids is not viable. Nucleic acid degradation can occur when nucleic acids are exposed to certain conditions, such as, elevated temperature, acidity, alkalinity, salt, preservatives, UV light, high pressure, to name a few.

DNA integrity is the wholeness or completeness of a cell's genomic and organelle-based DNA. After heat treatments, such as autoclaving, or other types of conditions that degrades a cell's nucleic acids, the cell's DNA integrity is reduced. The amount fragmentation (reduction in integrity) can be measured globally and is used as a time/temperature integrator. One can measure the integrity of either intrinsic DNA or extrinsic DNA to determine the amount of inactivation of the hazardous biological material.

Hazardous biological material is any biological material that could harm an animal if the animal ingests the biological material or, if placed on or inside the animal. Hazardous biological material include, but are not limited to, toxins, viruses, parasites, fungi, bacteria, spores (bacterial, fungal or parasitical), other types of pathogens, and cancer cells.

Mitochondria are "power-house" organelles found in multiple numbers in all cells of eukaryotes, and each mitochondrion possesses its own genome in multiple copies. Mitochondrial DNA contains polynucleotide sequences that are species-specific or family-specific. In addition, the mitochondrial genome also contains polynucleotide sequences that are highly conserved in many eukaryotic plants or animals. These properties make mtDNA sequences excellent targets for amplification in terms of specificity, sensitivity and robustness in addition to the fact that multiple copies per cell (>1,000) exist. Therefore, the advantages of targeting mtDNA with qPCR are substantial.

All mtDNA qPCR assays for this invention meet MIQE Guidelines (Bustin, et al., *Clinical Chem.* 55:611-622 (2009)) or Minimum Information for publication of Quantitative real-time PCR Experiments which features a quality control checklist on sample processing, nucleic acid extraction, target amplicon specifications, reaction optimization, specificity of reaction, internal amplification controls (IAC), calibration curves with calculated PCR efficiency, linear dynamic range and data analysis including repeatability and statistical methods. This approach to monitoring food safety and cleaning of objects, in general, represents a paradigm shift by using qPCR to quantify the disappearance of mtDNA over time caused by thermal or microwave processing and correlating the degradation rates closely to the thermal death time (D) of spore-forming bacteria. This method also involves correlating the thermal death time (D) of the bacteria, as determined by culture methods, to the destruction of mtDNA of the thermally- or microwave-processed foodstuff. Assessing mtDNA decomposition over time can also be used to assess shelf life of a food and the level of inactivation of biological material on or in medical equipment, empty or filled food containers, or other items.

The mtDNA qPCR assays of this invention are adjusted to highly correlate to D values (time required for 1 log reduction of pathogens at a certain temperature) according to the length of the amplicon, secondary DNA structure, annealing temperature, use of locked nucleic acids and primer/probe efficiencies.

As used herein, the term "about" and "approximately" refers to a quantity, level, value or amount that varies by as much as 30%, preferably by as much as 20%, and more preferably by as much as 10% to a reference quantity, level, value or amount. All cited prior art documents are incorporated by reference.

Figure 9:
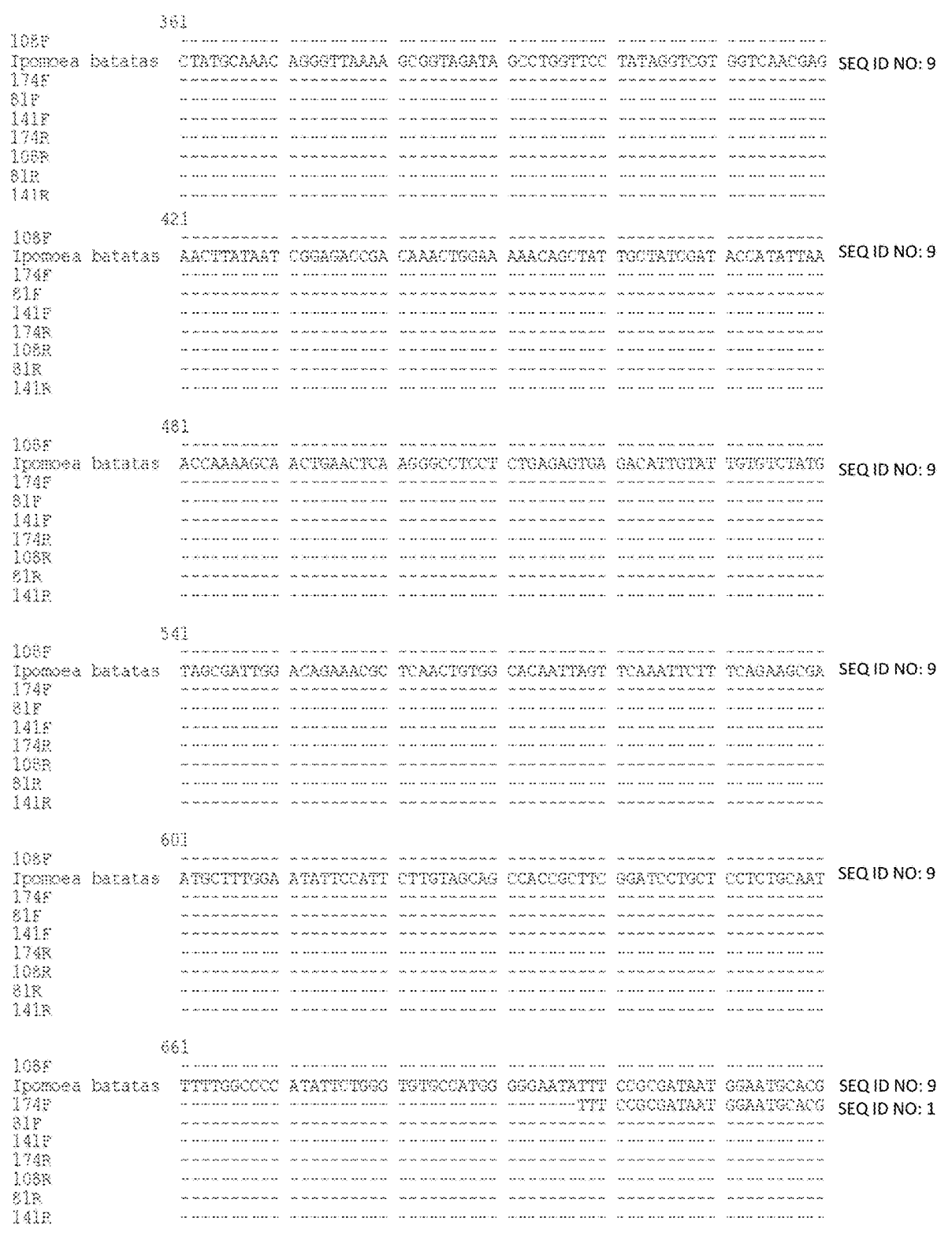

Example 1 Primers for Plant mtDNA Selection and Generation of Standardized Curves Primers are designed which use consensus sequences to target a wide variety of plant foods. Four sets of qPCR primers shown in Table 1 are designed with Primer Quest software (http://scitools.idtdna.com/Primerquest/) from Integrated DNA Technologies, Inc. (IDT) (Coralville, Iowa) targeting the *Ipomoea batatas* F1-ATPase alpha subunit (atp1) mitochondrial gene (GenBank AY596672.1). Amplicon length for each primer set is indicated by the number in the primer sets' name, 81 bp, 108 bp, 141 bp, and 174 bp. FIG. 9 shows the sequence of *I. batatas* atp1 (SEQ ID NO: 9), the location of the primers used, and the sequences of the amplicons generated. All primer sets match the *Ipomoea batatas* atp1 gene with 100% identity, and between approximately 95% and 100% identity for a wide range of common fruits, vegetables, and nuts (see Table 2 infra) when subjected to NCBI BLAST searches. Primers are purchased from IDT (Coralville, Iowa). Oligonucleotide primers are reconstituted in TE buffer (pH 7.5) and stored at −20° C. prior to use.

TABLE 1

| Primer name | Start Position | Sequence |
| --- | --- | --- |
| 174F (forward) | 698 | 5'-TTTCCGCGATAATGGAATGC ACGC-3' (SEQ ID NO: 1) |
| 174R (reverse) | 871 | 5'-TCCGATCGTTTAGCCGCTCT TTCT-3' (SEQ ID NO: 2) |
| 108F (forward) | 1133 | 5'-CGCCTTTGCTCAATTTGGCT CAGA-3' (SEQ ID NO: 3) |
| 108R (reverse) | 1240 | 5'-GGCAGTGGTGCATATTGTGG TTGT-3' (SEQ ID NO: 4) |
| 81F (forward) | 1133 | 5'-CGCCTTTGCTCAATTTGGCT CAGA-3' (SEQ ID NO: 5) |
| 81R (reverse) | 1213 | 5'-AGTACTTCTGTCAGCCTTGC ACCT-3' (SEQ ID NO: 6) |
| 141F (forward) | 87 | 5'-GAATTTGCCAGCGGTGTGAA AGGA-3' (SEQ ID NO: 7) |
| 141R (reverse) | 227 | 5'-TCCCGCAGGAACATCCACAA TAGA-3' (SEQ ID NO: 8) |

A test comparing autoclaved (steamed at 121° C. for 20 minutes) versus non-autoclaved sweet potato puree DNA is run with each primer set. Puree is generated prior to treatment by grinding the sweet potato and water in Waring blender until puree is formed. Sweet potato DNA is then isolated after treatment using MO BIO PowerSoil® DNA isolation kit (Carlsbad, Calif.) according to manufacturer's directions. qPCR is performed in 25 µl total volume with 2× IQ SYBR Green supermix (SYBR Green I dye, 50 U/ml iTaq DNA polymerase, 0.4 mM each of dATP, dCTP, dGTP and dTTP, 6 mM $MgCl_2$, 40 mM Tris-HCl, pH 8.4, 100 mM KCl, and 20 nM fluorescein (BioRad, Hercules, Calif.)), 300 nM final concentration each for forward and reverse primers listed in Table 1, sweet potato total DNA (5-10 ng/reaction), and qPCR water (Ambion, Austin, Tex.) to final volume. qPCR amplifications are performed in a MyiQ (BioRad, Hercules, Calif.) thermal cycler with the following conditions: 95.0° C. for 3 minutes; 40 cycles of 95.0° C. for 30 seconds, 60.0° C. for 30 seconds, 72.0° C. for 30 seconds; with FAM channel optics "on" during annealing stage. Negative control is performed without any DNA ("no template control" or "NTC"), substituting same volume of molecular grade water for DNA. Positive and normalizing controls are used for all assays. For a sample to be considered positive, its threshold cycle (Ct) value must be less than all negative control reactions, and the corresponding amplification curve has to exhibit the three distinct phases of real-time PCR: lag, linear and plateau.

All four primer sets produced amplicons of expected lengths (81 bp, 108 bp, 141 bp, and 174 bp) when run in 1% agarose gels. All amplicons are isolated and sequenced, and each amplicon exhibits 100% identity to the *Ipomoea batatas* atp1 mitochondrial gene under NCBI BLAST analysis as well as atp1 in many other plants. The sequence of the 174 bp amplicon generated by 174F and 174R primers is SEQ ID NO: 14. The sequence of the 108 bp amplicon generated by 108F and 108R primers is SEQ ID NO: 15. The sequence of the 81 bp amplicon generated by 81F and 81R primers is SEQ ID NO: 16. The sequence of the 141F and 141R primers is SEQ ID NO: 17. Of the four primer pairs assayed, primer set 174 exhibits the greatest difference in Ct values between the two samples, autoclaved sweet potato and unautoclaved control sweet potato (9 Ct difference versus 8, 5 & 5 for amplicon lengths of 141, 108, and 81 base pairs, respectively). This result is understandable as longer amplicons are statistically more likely to experience degradation than shorter ones. As such, of these four sets of primer pairs, 174F and 174R, provides better results compared to the other three primer sets and, thus, is used in the other examples described infra. However, this invention is not limited to the above listed primers. Any other primer set that has high identity to atp1 and which yields an amplicon of between approximately 80 bp to approximately 250 bp can be used for fruits, vegetable, and nuts. In another embodiment, the primer set for assaying fruits, vegetable and nuts generates an amplicon within atp1 ranging from approximately 100 bp to approximately 200 bp. In yet another embodiment, the primer set for assaying fruits, vegetable and nuts generates an amplicon within atp1 ranging from approximately 125 bp to approximately 175 bp. It is also helpful that the primer set used for any food matrix or medical device generates a Ct difference of approximately 9 or greater between the negative control (unprocessed sample) and processed sample.

Standard curves are generated using double-stranded, sequence-verified oligonucleotides of the *I. batatas* atp1, having the same sequence as the amplicon generated by the 174F and 174R primers (SEQ ID NO: 14) (gBlocks® gene fragments purchased from IDT (Coralville, Iowa)). Ten-fold serially dilutions of atp1 amplicon copies ($10^7$ to $10^1$) are performed, qPCR is performed using the protocol above with 174F and 174R primers. PCR amplification efficiency (E) is determined using the slope of the standard curve: $E=(10^{-1/slope})-1$. Data analysis of the qPCR standard curve is performed using goodness-of-fit linear regression correlation coefficient ($R^2$). The slope value is used to assess the robustness of the assay using the efficiency value above. The amplification efficiency is calculated as 106%, $R^2=0.9884$ (see FIG. 1).

Bustin, et al. (2009) published the MIQE guidelines (Minimum Information for publication of Quantitative real-time PCR Experiments) to facilitate assessment and evaluation of new, clinical qPCR assays. The guidelines include a checklist for authors, reviewers and editors to help them ensure the integrity of scientific literature and promote consistency between laboratories (Bustin, et al. (2009)). According to the guidelines, essential information includes experimental design, sample description and processing, nucleic acid extraction, qPCR target information, qPCR oligonucleotides, qPCR protocol, qPCR validation, and data analysis. The present invention meets all essential information requirements.

Example 2 Hot Oil Bath as Substitute for Industrial Microwave System

A hot oil bath (EW-111, Neslab Instruments, Newington, N.H.) filled with 8 L white mineral oil (Therminol XP, Solutia, Inc, St. Louis, Mo.) is used to maintain a temperature of 121.1° C. for substances placed in a thermal death tube (TDT). A thermal death tube allows one to replicate the conditions of an industrial microwave system yet still obtain samples of the substance at various time points. 100 µl sweet potato (SP) puree in 1:4 dilution with 0.9% saline or 100 µl of *Geobacillus stearothermophilus* (GS) spores (ca. $10^8$ CFU/ml) are inserted into separate TDTs and are sealed according to instructions. Samples are heated for 0, 0.5, 1, 2, 4, 8, 16 and 20 minutes at 121.1° C., taking into account the 30 seconds come up time (CUT). Three repetitions are run per time point; three TDTs are placed in a metal tea strainer to facilitate removal of samples from hot oil. Strainers containing TDTs are taken out of oil bath and immediately placed in an ice slurry for 30 seconds to quickly cool them. Strainers are stored at room temperature until ready for DNA extraction or culture plating. Total amount of sweet potato puree recovered from hot oil bath treatment ranges between approximately 50 µl to approximately 75 µl from an initial sample of 100 µl (see FIG. 2).

GS spores are serially diluted with 0.9% saline solution and plated with a spiral plater (Spiral Biotech, Inc., Norwood, Mass.) on BHI agar (Becton Dickinson, Sparks, Md.). After 24 hours incubation at 55° C., colonies are enumerated with an automated spiral plate counter (Q-count, Spiral Biotech Inc. Norwood, Mass.). The lower detection limit is $10^2$ CFU/ml. Another *G. stearothermophilus* indicator system, the Prospore ampoule (Mesa Laboratories, Inc, Lakewood, Colo.) are incubated at 55° C. for 48 hours, and then checked for color change as directed.

Treated sweet potato puree is removed from TDT and placed directly into a MO BIO bead beater tube (Carlsbad, Calif.). The MO BIO PowerSoil® DNA isolation kit (Carlsbad, Calif.) is used according to manufacturer's recommendations to extract sweet potato DNA from the treated puree. Total DNA samples are analyzed by spectrophotometer (Nanodrop, Wilmington, Del.) for quantity and quality. For qPCR, DNA is normalized by concentration: between 5-10 ng/µl per reaction.

qPCR is performed in 25 µl total volume with 2×IQ SYBR Green supermix (SYBR Green I dye, 50 U/ml iTaq DNA polymerase, 0.4 mM each of dATP, dCTP, dGTP and dTTP, 6 mM $MgCl_2$, 40 mM Tris-HCl, pH 8.4, 100 mM KCl, and 20 nM fluorescein (BioRad, Hercules, Calif.)), 300 nM final concentration each for 174F and 174R primers, sweet potato DNA (5-10 ng/reaction) and qPCR water (Ambion, Austin, Tex.) to final volume. qPCR amplifications are performed in a MyiQ (BioRad, Hercules, Calif.) thermal cycler with the following conditions: 95.0° C. for 3 minutes; 40 cycles of 95.0° C. for 30 seconds, 60.0° C. for 30 seconds, 72.0° C. for 30 seconds; with FAM channel optics "on" during annealing stage. No template control (NTC) and positive controls are used for all assays. A positive control is used to normalize data between assays. For a sample to be considered positive, its threshold cycle (Ct) value must be less than all negative control reactions, and the corresponding amplification curve has to exhibit the three distinct phases of real-time PCR: lag, linear and plateau.

Figure 2:
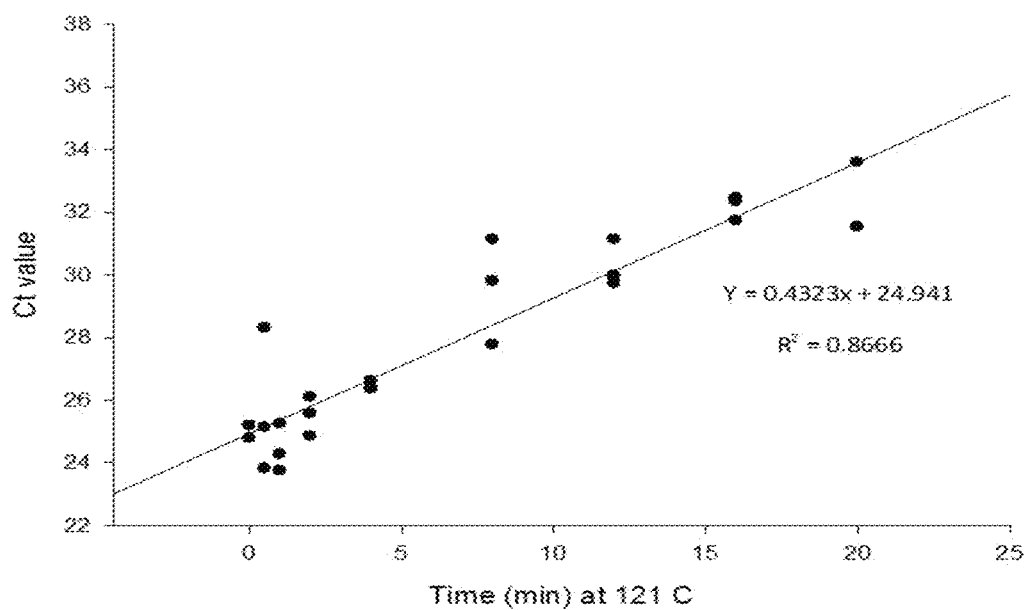
FIG. 2 illustrates the effect of hot oil bath (at 121° C.) on sweet potato puree mtDNA fragmentation (increase in Ct value) over time.
Figure 3:
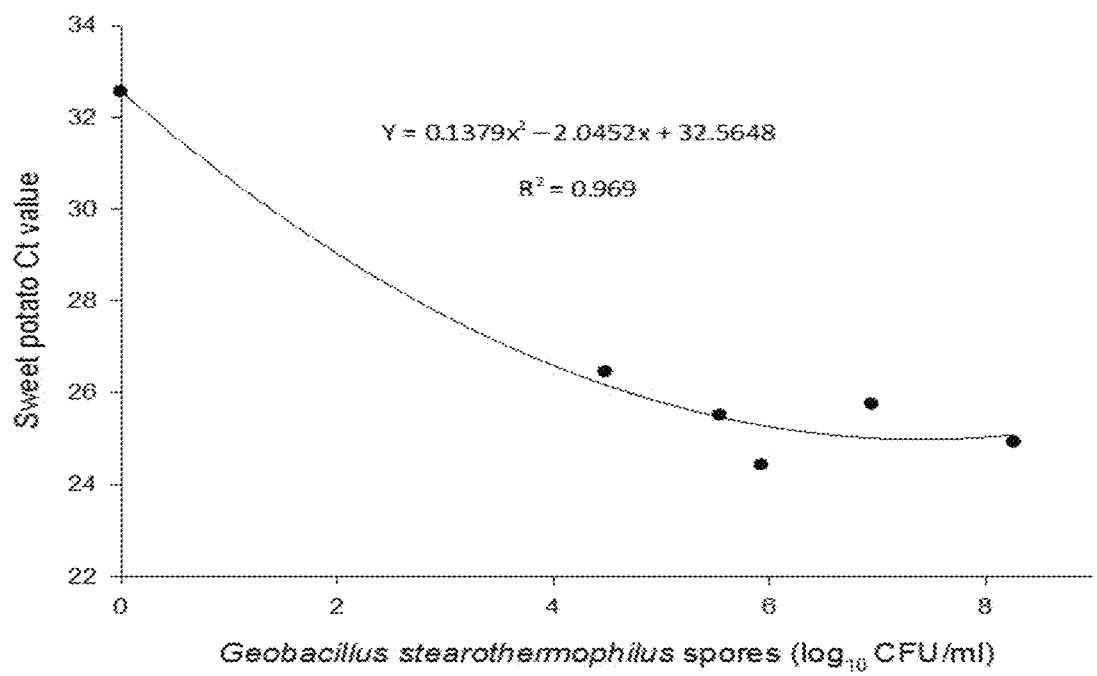
FIG. 3 illustrates the high correlation between surrogate GS spore destruction and increase in Ct value of sweet potato puree mtDNA over time for the hot oil assay (121° C.).

FIG. 2 illustrates the effect of hot oil bath (at 121° C.) on sweet potato puree mtDNA fragmentation (increase in Ct value) over time. In the hot oil bath, Ct value increased from approximately 24 at time zero to between approximately 30 and approximately 32, a 6-8 unit increase. This hot oil bath assay exhibits a high correlation ($R^2$=0.97) between surrogate GS spore destruction and increase in Ct value over time (see FIG. 3).

Example 3 Autoclave Degradation of Sweet Potato mtDNA and *G. stearothermophilus* Spores To determine if mtDNA also fragments during the high heat and pressure of autoclaving, and assess the level of degradation of the DNA, sweet potato puree and *G. stearothermophilus* spores are assayed in a laboratory autoclave (Amsco Eagle SG-3021 Scientific Gravity Sterilizer, Steris Corp., Mentor, Ohio). The autoclave is programmed to run liquid sterilizing times of 2, 4, 8 and 20 minutes at 121° C. Come up times (initial CUT=5 minutes, all others=1 minute) and come down times (Exhaust=11:53 to 13:25 minutes) are similar for all runs. In a plastic micro-centrifuge holder three samples are included per run: 300 mg sweet potato puree (prepared as described supra), 250 µl *G. stearothermophilus* spores (log 8 CFU/ml) (prepared as described supra) both samples in 1.5 ml micro-centrifuge tubes containing a small hole in the top to vent water vapor, and one commercial *G. stearothermophilus* vial (Prospore, Mesa Laboratories, Inc, Lakewood, Colo.). Vent holes are then covered with parafilm. After autoclave treatment, sample tubes are placed on ice until they cool to room temperature. DNA is extracted from each sample using the PowerSoil® DNA isolation kit (MO BIO, Carlsbad, Calif.) using manufacturer's recommendations. DNA is quantified and qualified via spectrophotometry (Nanodrop, Wilmington, Del.). *G. stearothermophilus* spores are serially diluted as described supra and are plated with a spiral plater (Spiral Biotech, Inc., Norwood, Mass.) on BHI agar (Becton Dickinson, Sparks, Md.). After 24 hours incubation at 55° C., colonies are enumerated with an automated spiral plate counter (Q-count, Spiral Biotech, Inc., Norwood, Mass.). The lower detection limit is $10^2$ CFU/ml. Prospore ampoules (Mesa Laboratories, Inc, Lakewood, Colo.) are incubated at 55° C. for 48 hours, and then checked for indicator colors. qPCR is performed using the above described methods.

Figure 4:
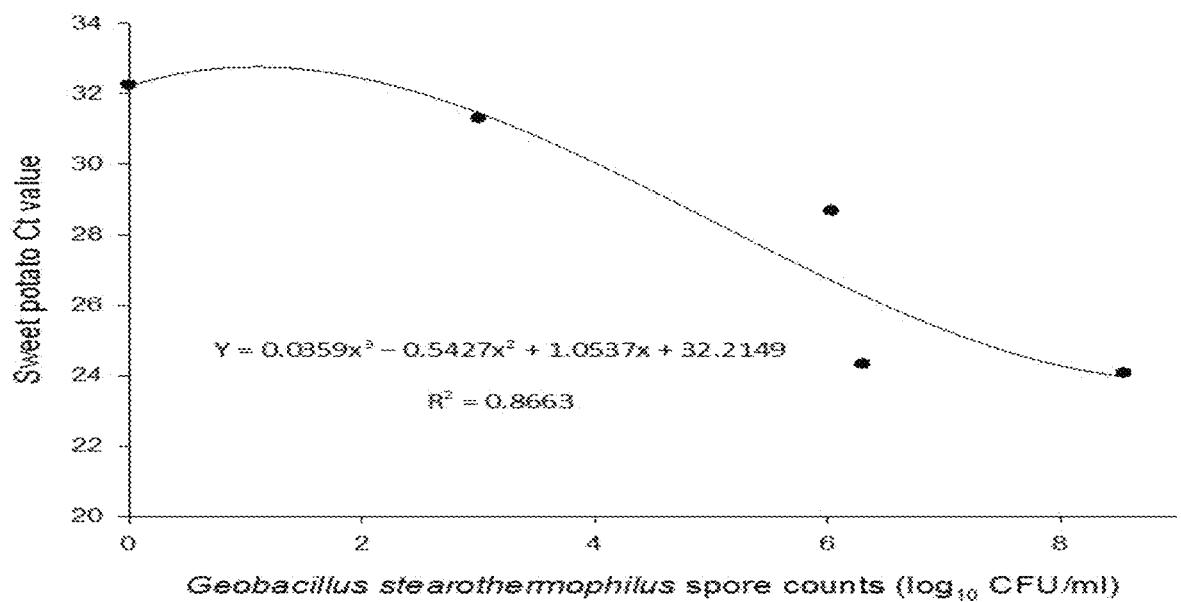
FIG. 4 illustrates the high correlation ($R^2=0.87$) between surrogate *G. stearothermophilus* spore destruction and increase in Ct value over time when the sweet potato puree and *G. stearothermophilus* spore are autoclaved (121° C.).

In the autoclave treatment, Ct value for sweet potato puree mtDNA increases from approximately 25 at time zero to 32 after 20 minutes. Ct value increase is similar in the autoclave treatment which is conducted using the same time/temperature profile as the oil bath. The autoclave assay exhibits a high correlation ($R^2$=0.87) between surrogate *G. stearothermophilus* spore destruction and increase in Ct value over time (see FIG. 4)

Example 4 Assaying mtDNA Degradation on Various Heat Processed Food Substances

The atp1 gene is found to be highly conserved among plant species. As described above, BLAST analysis of the 174 forward and reverse primers reveals that they exhibit 100% identity with a wide variety of fruits, nuts and vegetables. To assess if the 174 primers can be used universally to test plant-based foods, both singly and in mixtures such as soups, the following experiment is performed. Fresh, uncooked fruits, vegetables and nuts (see Table 2 for items) are purchased from a retail grocery store. The samples are processed immediately by grinding in a Hamilton Beach coffee mill. The coffee mill is thorough cleaned with distilled water and 70% ethanol between samples and repetitions to prevent DNA cross-contamination. For each variety of plant tested, three separate samples of that plant are used. Six repetitions are tested in all, three uncooked controls and three autoclave treatments (20 minutes at 121° C. using procedure described above). The tissue culture protocol of the MasterPure DNA purification kit (Epicentre, Madison, Wis.) is used according to manufacturer's recommendations. DNA is quantified and qualified using a spectrophotometer (Nanodrop, Wilmington, Del.). DNA is normalized to 5-10 ng/well and undergo qPCR assays using the 174F and 174R primers and the protocol described above. Each sample is run in duplicate wells. DNA is saved at –20° C. in case amplicon sequencing is required. Mean Ct values for uncooked and autoclaved plant materials are recorded as well as the increase of Ct caused by autoclave treatment and the slope of the line formed by the graph of the two values. The results are presented in Table 2.

TABLE 2

| Sample | Mean uncooked Ct | Mean autoclaved Ct | Difference | Slope |
|---|---|---|---|---|
| Vegetables | | | | |
| White potato | 19.73 | 32.77 | 13.04 | 0.65 |
| Sweet potato | 24.06 | 33.00 | 8.90 | 0.45 |
| Tomato | 18.86 | 32.27 | 13.41 | 0.67 |
| Green pepper | 19.45 | 35.66 | 16.21 | 0.81 |
| Red pepper | 18.99 | 34.63 | 15.65 | 0.78 |
| Jalapeno pepper | 19.96 | 35.66 | 15.70 | 0.79 |
| Carrot | 15.71 | 32.45 | 16.74 | 0.84 |
| Green bean | 22.45 | 32.38 | 9.93 | 0.50 |
| Corn | 22.40 | 27.24 | 4.84 | 0.24 |
| Cucumber | 18.47 | 29.88 | 11.40 | 0.57 |
| Biofuels | | | | |
| Switch grass | 28.26 | 34.69 | 6.43 | 0.32 |
| Fruits | | | | |
| Apple | 22.95 | 36.27 | 13.32 | 0.67 |
| Blueberry | 25.88 | 35.51 | 9.63 | 0.48 |
| Peach | 20.93 | 37.52 | 16.60 | 0.83 |
| Strawberry | 23.27 | 33.17 | 9.90 | 0.50 |
| Pineapple | 22.97 | 33.31 | 10.35 | 0.52 |
| Grape | 27.95 | 32.11 | 4.16 | 0.21 |
| Nuts | | | | |
| Peanut* | 17.00 | 23.10 | 6.10 | 0.32 |
| Almond | 18.31 | 27.25 | 8.94 | 0.45 |
| Pecan | 25.86 | 31.43 | 5.57 | 0.28 |

*Roasted at 167° C. for 19 min. All others autoclaved at 121° C. for 20 min.

Using the 174F and 174R primers, a significant, detectable increase in Ct value (approximately 4 to approximately 17 units) is found between uncooked and autoclaved samples (121° C. for 20 minutes) for the vegetables, fruits and nuts listed in Table 2. Therefore, the 174F and 174R primers are be suitable for quantifying heat treatment efficacy and quality in a wide variety of plant foods, in complex mixtures such as soups, and plant precursors for biofuels. Not wishing to be bound to any particular hypothesis, Ct differences that occur between different foods may result from differences in DNA extraction because some plant foods are high in sugars or fats, while other plant foods are high in fiber.

Example 5 mtDNA Degradation in Acidified Food Substances

Figure 5:
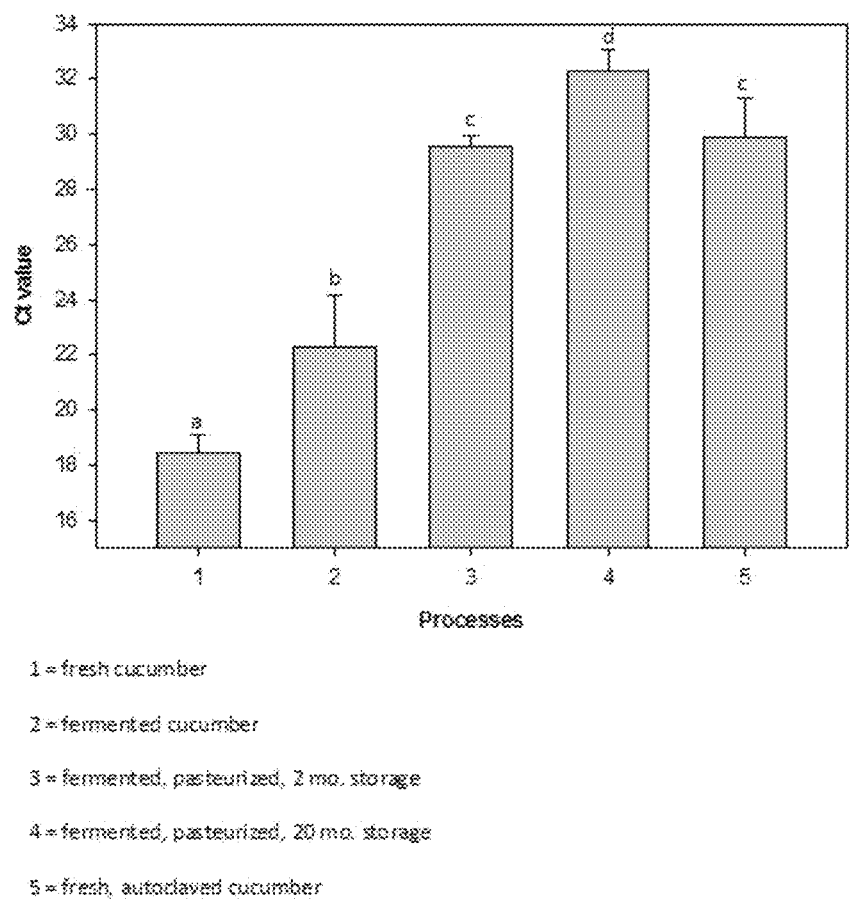
FIG. 5 illustrates the change in Ct value indicating mtDNA fragmentation of cucumbers during pasteurization (75° C. for 15 minutes), fermentation and storage compared to Ct values of cucumbers in autoclave treatment (121° C.).

Determining mtDNA fragmentation can assess shelf life in vegetable products. Cucumbers and hamburger dill chips are assayed during processing and storage (FIG. 5). Cucumbers are fermented in NaCl for 8 months, are pasteurized at 75° C. for 15 minutes and then are stored at room temperature. Using the qPCR protocol and the 174F and 174R primers, both described supra, mtDNA fragmentation at pre-fermentation, immediately after pasteurization, at 2 months, and at 20 months is assayed. mtDNA fragmentation of autoclaved cucumbers is performed for comparison using the protocols provided above. Threshold cycle (Ct) values are significantly different between all treatments, except between a fermented and pasteurized cucumber stored for 2 months and an autoclaved cucumber. There is a significant difference (student t-test, P<0.05) between the pickles stored at 2 and 20 months. The fermented, pasteurized pickle has a similar Ct value as the autoclaved cucumber. The results demonstrate that lower thermal processes (75° C. for 15 minutes) under acidified conditions (pH=3.8) yield similar mtDNA fragmentation results to more elevated temperature conditions (121° C.) and that thermal processes under 100° C. with high acid products can be monitored for the reliability of the heat treatment, acidification and/or fermentation using qPCR of mtDNA.

Example 6 mtDNA Degradation in Dry Roasted Peanuts

To demonstrate that mtDNA degradation is an effective time/temperature integrator for roasted solid foodstuffs such as nuts, Virginia green runner peanuts are spiked with $10^8$ CFU/g *Enterococcus faecium* (ATCC 8459; a *Salmonella* surrogate) and compared with Ct values of the same peanut samples (not spiked with *E. faecium*) during dry roasting at 167° C. *E. faecium* is inoculated into BHI broth (Remel, Lenexa, Kans.) from freshly plated colonies and incubated statically overnight at 35° C. Cultures are concentrated 2× by centrifugation (5810R, Eppendorf, Hamburg, Germany) at 6,000 rpm for 10 minutes at 4° C. and resuspended in 0.5× initial volume with sterile 0.9% saline. Target concentration is $10^8$ CFU/ml. Initial culture concentration is determined by spectrometry at $A_{600}$ and a simplified agar plate technique (Jett, et al., *BioTechniques* 23:648-650 (1997)) utilizing square petri dishes and the track-dilution method. *E. faecium*-inoculated saline is added to the total weight of peanuts to be tested in a large plastic zipper bag, diluting the culture 1:20. The bag is closed and secured. Contents are mixed thoroughly, and then sit for 5 minutes to absorb the liquid. Inoculated peanuts are poured onto wire racks in 100 g aliquots and allowed to air dry for 20 minutes.

A convection oven (Despatch Model LXD1-42-2; Minneapolis, Minn.) is set to 167° C. and is allowed to equilibrate for 30 minutes. A metal rack is inserted in the oven and is brought to temperature. This rack holds smaller racks made of hardware cloth through which peanuts do not pass. Each batch consists of 100 g of peanuts laid out on the small hardware cloth racks. When the smaller racks are inserted into the larger rack, the peanuts are essentially suspended in the moving air inside the oven. For each roasting batch, the oven door is quickly opened, the tray with the peanuts is slid into the large rack, and the door of the oven quickly closed. There is a drop in the oven temperature caused by the door opening. The lowest temperature reached and the number of seconds required for the oven to return to set point are recorded for each batch. At the appropriate time point, the oven is opened quickly, and peanuts are removed in the small rack. This rack is placed over a homemade cooler with sufficient flow to cool the peanuts to room temperature in 30 seconds. To prevent cross contamination between repetitions, a clean gloves are used for loading each batch into the small rack and into the oven, and clean gloves are used to remove each batch. Between runs, the small rack and the cooler are sprayed with 70% ethanol and allowed to dry thoroughly before the next batch comes into contact with them. Cooled peanuts are placed in plastic bags and stored until ready for mtDNA analysis and *E. faecium* plate count analysis. It is acknowledged that while the oven used for this experiment has convective airflow, the oven is not comparable to industrial-scale, commercial ovens used for peanuts. However, it is assumed that the results would be similar when an industrial-scale, commercial oven is used.

Three replicate samples are taken from the following time points: 0, 3, 6, 9, 12, 15, 18, and 21 minutes. Ten grams are taken from each 100 g replicate and placed in a stomacher bag (Filtra-bag, Fisher, Pittsburgh, Pa.) with 10 ml sterile 0.9% saline (1:1 dilution). Peanuts are stomached in a Seward Stomacher 400 (Tekmar, Cincinnati, Ohio) for 2 minutes at normal speed. Filtrate is aseptically removed from the stomacher bag, serially diluted and plated as described above using the simplified agar plate technique (Jett, et al. (1997)) with BHI agar (BD, Sparks, Md.). Plates are incubated at 35° C. over-night. Plates are counted manually, and CFU/g peanuts are calculated, taking into account concentration and dilution factors.

Figure 6:
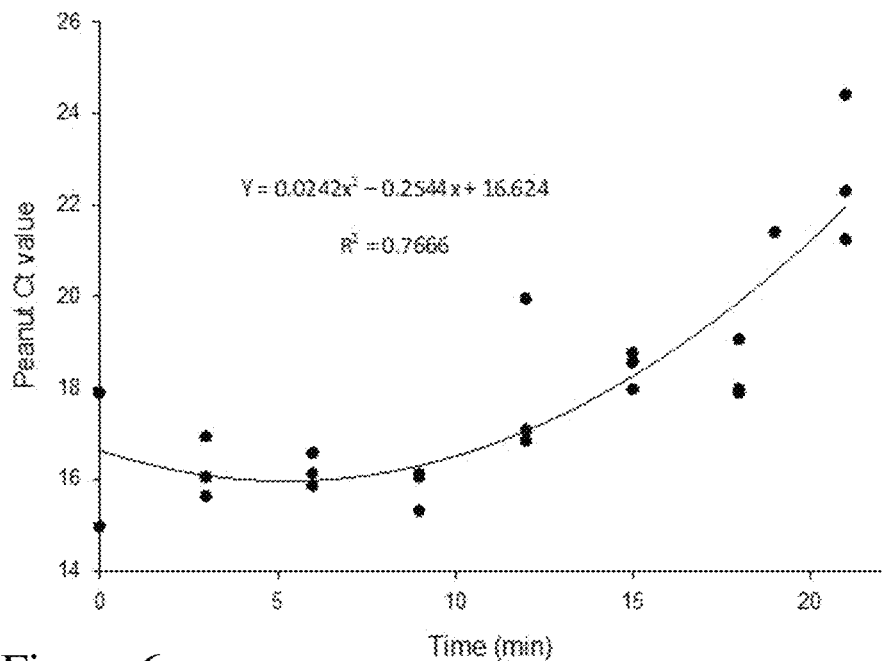
FIG. 6 illustrates the mtDNA degradation (increase in Ct value) of peanuts dry roasted (167° C.) at the indicated time intervals.
Figure 7:
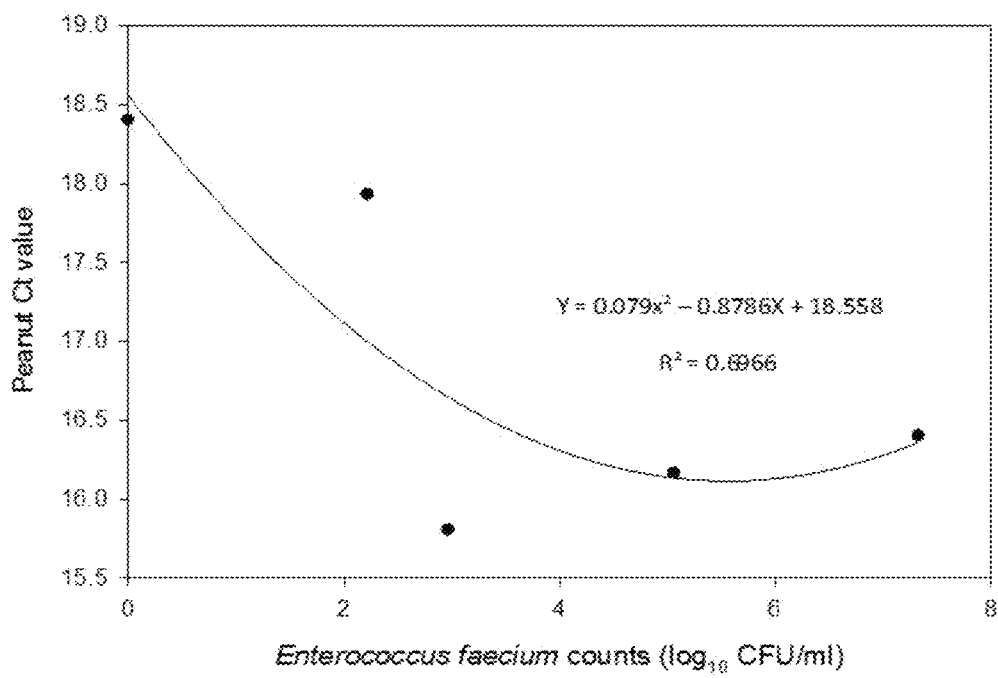
FIG. 7 illustrates the correlation between mtDNA degradation (increase in Ct value) in dry roast treatment of peanuts (167° C.) and survival of a *Salmonella* surrogate, *E. faecium* ($\log_{10}$ CFU/ml).

Three peanuts from each replicate are ground under liquid nitrogen in a mortar and pestle. The mortar and pestle are thoroughly cleaned between samples with 70% ethanol to prevent cross contamination. DNA is extracted using ca. 2.5 mg or one inoculation loop of ground peanut in the MasterPure DNA purification kit (Epicentre, Madison, Wis.) using the tissue sample portion of the protocol. DNA is quantified and qualified with a spectrophotometer (Nanodrop, Wilmington, Del.).

qPCR is performed in 25 µl total volume with 2×IQ SYBR Green supermix (SYBR Green I dye, 50 U/ml iTaq DNA polymerase, 0.4 mM each of dATP, dCTP, dGTP and dTTP, 6 mM $MgCl_2$, 40 mM Tris-HCl, pH 8.4, 100 mM KCl, and 20 nM fluorescein (BioRad, Hercules, Calif.)), 300 nM final concentration each for 174 forward and 174 reverse primers, peanut DNA (5-10 ng/reaction) and qPCR water (Ambion, Austin, Tex.) to final volume. Amplifications are performed in a MyiQ (BioRad, Hercules, Calif.) thermal cycler with the following conditions: 95.0° C. for 3 minutes; 40 cycles of 95.0° C. for 30 seconds, 60.0° C. for 30 seconds, 72.0° C. for 30 seconds; with FAM channel optics "on" during annealing stage. No template control (NTC) and positive controls are used for all assays. The positive control is used to normalize data between assays. For a sample to be considered positive, its threshold cycle (Ct) value must be less than all negative control reactions, and its corresponding amplification curve must exhibit the three distinct phases of real-time PCR: lag, linear and plateau. Ct values are initially steady, then increase after 12 minutes of roasting to a mean value approximately 22 units after 21 minutes (see FIG. 6). Peanut mtDNA fragmentation is correlated to *E. faecium* death because $R^2=0.67$ (see FIG. 7).

Figure 8:
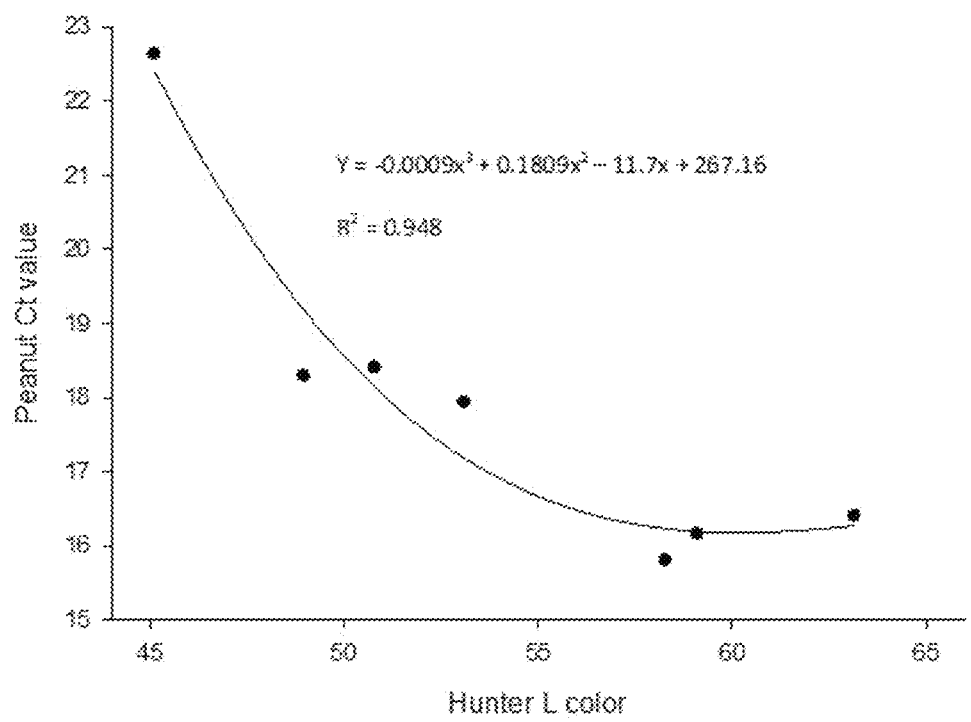
FIG. 8 compares mtDNA degradation (increase in Ct value) of dry roasted peanuts (167° C.) with the Hunter L color, a roasting quality indicator.

The remainder of each batch of peanuts is used to determine the Hunter L value color. The skins are removed from approximately 40 g peanuts which are placed in a glass petri dish and inserted above a calibrated HunterLab DP9000 with D25 sensor (Hunter Associates Laboratory, Reston, Va.) utilizing the Lab scale (a standardized color scale). Readouts are recorded three times per sample with the peanuts removed and resorted in the petri dish between readings with the peanuts placed outer-side down, if broken. The color is expressed as the mean of the three replications for each peanut sample presented to the colorimeter. The scale of the readings range from 1 to 100 with 1 representing black and 100 representing white. Peanut mtDNA fragmentation is a good correlation to Hunter L color (see FIG. 8), a quality parameter used to determine roasting endpoint because $R^2=0.95$.

Experiment 7

Using of Fluorescent Probe with Hot Oil Bath as Surrogate for Industrial Microwave System The protocol of Experiment 2 is repeated except instead of using SYBR Green I dye (an intercalater of DNA), a nucleic acid probe such as TaqMan® is used to measure the amount of mtDNA degradation. TaqMan® probes contain a fluorescent reporter dye (e.g., 6-carboxyfluorescein (6-FAM™) or tetrachloro-6-carboxy-fluorescein (TET)) at the 5' end and a quencher dye at the 3' end (e.g., Iowa Black FQ or Black Hole Quencher (BHQ-2) quenchers). For TaqMan® detection, during each amplification cycle the probe attaches along with the primers to the target sequence of DNA to be copied. As the DNA strand is copied, the reporter dye is released from the probe sequence, and its fluorescent signal is measurable because it is no longer near the quencher dye. The amount of fluorescence increases with each PCR cycle in proportion to the amount of target DNA amplified, thereby allowing direct detection and quantification of the target DNA sequence with a high degree of specificity, accuracy, and sensitivity. The probe's sequence can range from approximately 15 bp to approximately 30 bp and is the sequence of the coding or non-coding strand (reverse complement of the coding strand sequence) of the amplicon.

The GS spores and sweet potato are processed according to the protocol in Experiment 2. The fluorescence of the samples is measured, and the Ct values obtained are almost identical to the values obtained in Experiment 2.

While the above experiments examined the Ct value of atp1 from mtDNA, one can determine the Ct value of any mtDNA. One can pick any primers that generate a desired amplicon of approximately 250 bp or less during the DNA amplification step.

Figure 10:
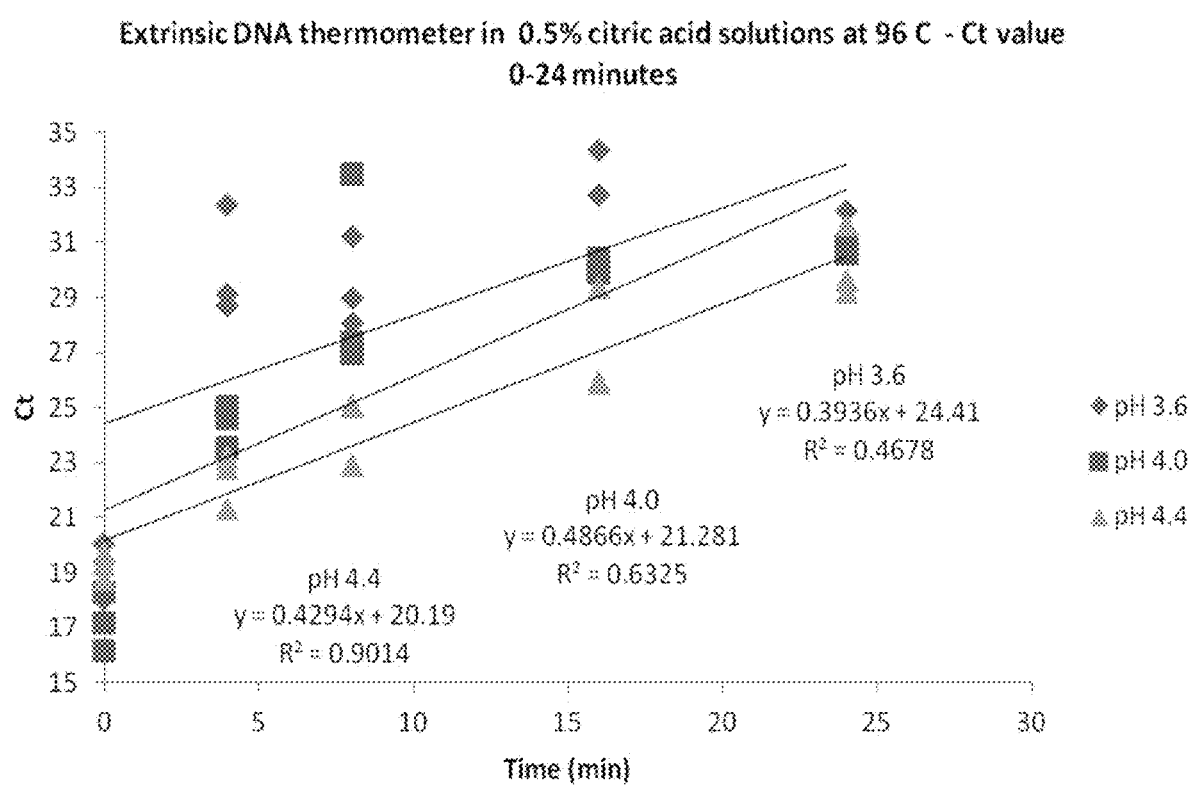
FIG. 10 shows the extrinsic DNA thermometer at three different pH levels from 0-24 minutes at 96° C.
Figure 11:
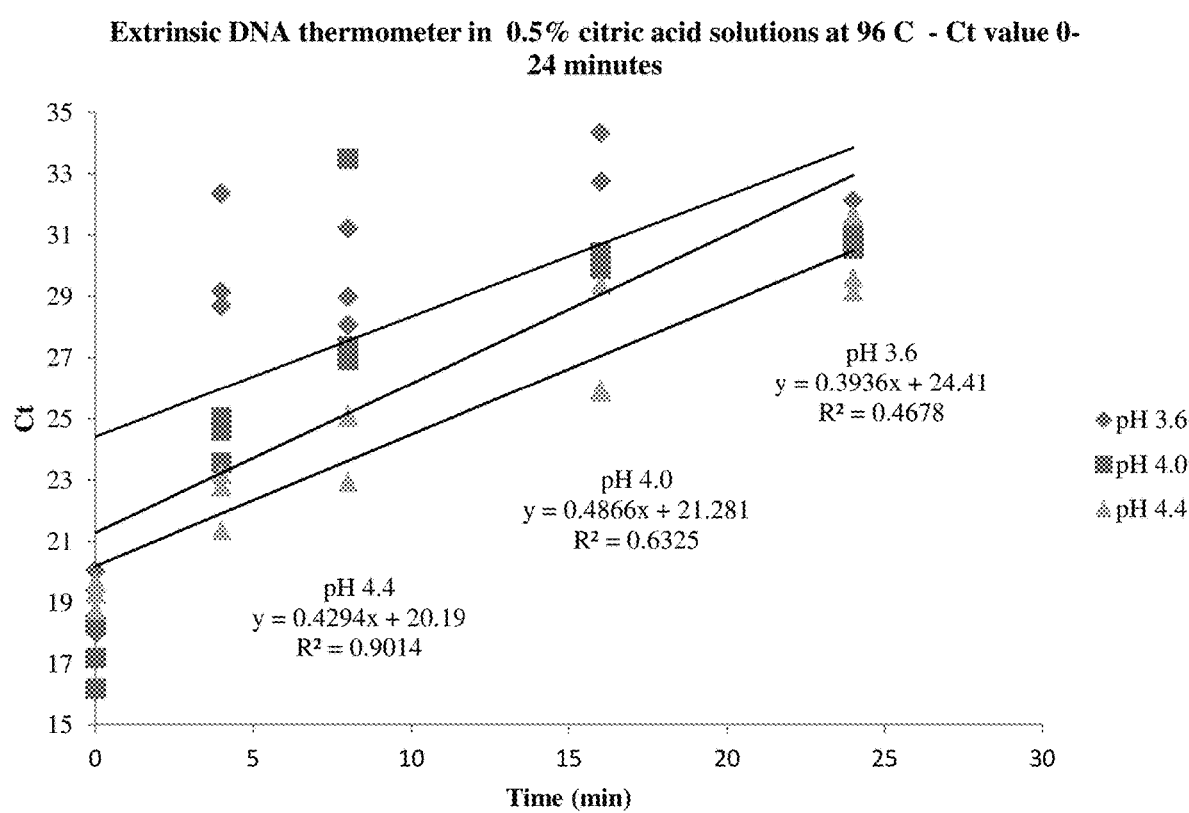
FIG. 11 shows the extrinsic DNA thermometer at three different pH levels from 0-5 minutes at 96° C.

Example 8 Extrinsic DNA Thermometer Testing the Efficacy of Pasteurization and Other Thermal Processes This experiment demonstrates the use of extrinsic DNA as a time/temperature indicator for inactivation of hazardous biological material when one does not want or cannot perform qPCR on intrinsic DNA. One example of using this type of assay is to assess the efficacy of inactivation of hazardous biological material on a food container (e.g., a jar) or a medical device. Extrinsic DNA thermometers (described infra) are time/temperature indicators which are added and recovered from thermal processing or other inactivation processing methods for foods, packaging, and medical equipment to test the efficacy of the inactivation system and/or method. A solution is prepared containing 0.5% citric acid and divided into three aliquots. Each aliquot is adjusted to either pH 3.6, 4.0 or 4.4 using 1M NaOH. All solutions are filter sterilized by passage through 0.45 um filters. An extrinsic DNA thermometer is created by combining 2 µl of $10^8$ copies/µl of the 174 primer amplicon for atp1 (SEQ ID NO: 14) (gBlock® gene fragment purchased from IDT, Coralville, Iowa) (see FIG. 1) with 18 µl of a citric acid solution in a 200 µl domed thermal cycler tube. Final concentration of extrinsic DNA in each tube is $10^7$ copies/µl. Tubes are placed in a thermal cycler (MyiQ, BioRad, Hercules, Calif.) when the temperature reaches 96° C. Samples are removed at time points 0, 4, 8, 16, 24 minutes in assay 1; and 0, 1, 2, 3, 4, 5 minutes in assay 2; with three reps at each time point using three different pH levels. Total number of samples is 45 each for each assay. After heat treatment, samples are placed in ice water slurry until cool, approximately 10 minutes. Atp1 qPCR protocol is run on each sample as described supra using 174F and 174R primers, being careful to segregate amplicon from reagents and pipettemen. FIGS. 10 and 11 show Ct values of extrinsic DNA thermometer, consisting of gBlock® of atp1 amplicon (SEQ ID NO: 14) in 0.5% citric acid, versus time at 96° C. FIG. 10 runs from 0-24 minutes, FIG. 11 from 0-5 minutes. For longer time courses, pH 4.4 had the best goodness-of-fit value (FIG. 10: $R^2$=0.90). For shorter thermal processes, 5 minutes or less at 96° C., pH 4.4 had the best goodness-of-fit (FIG. 11; $R^2$=0.67). Extrinsic DNA thermometers can be used in low temperature/low acid thermal processes, medical or container applications, or any process where intrinsic DNA is difficult to obtain.

While a citric acid solution to hold the extrinsic DNA is used in this example, one can use any organic acid or inorganic acids to generate a low pH solution into which extrinsic DNA is placed. A non-limiting example of an organic acid is malic acid. Non-limiting examples of inorganic acids are HCl and phosphoric acid. Further, while this example used atp1 amplicon having SEQ ID NO: 14, any double stranded DNA of between approximately 80 bp and approximately 250 bp (contiguous bp) of atp1 or any mitochondrial DNA can be used with the appropriate primers to generate an amplicon of the sequence used. Also a labeled probe can be used into of an intercalating dye as per the above protocol.

One can use extrinsic DNA to determine the efficacy of inactivation of a hazardous biological material in a food matrix, instead of analyzing intrinsic DNA. One simply needs to submit an amount of extrinsic DNA to the processing methods of the food matrix and then determine the Ct of the extrinsic DNA. The extrinsic DNA may need to be placed in a container.

Figure 12:
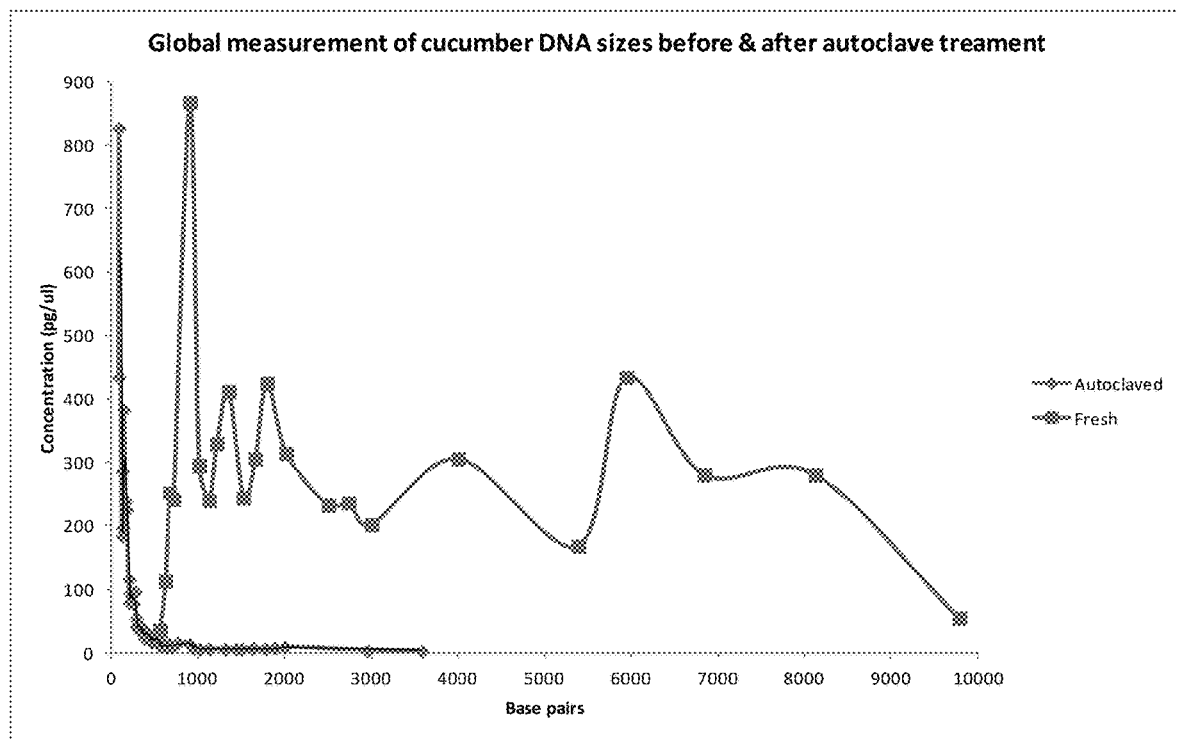
FIG. 12 illustrates the fragmentation and reduction of total DNA integrity caused by autoclave treatment by comparing size and concentrations of cucumber DNA globally.

Example 9 Using Total DNA Fragmentation of Plant Food Matrix During Thermal Processing as a Measure of Processing Efficacy DNA samples from previous described assays and similar concentrations (approximately 200 ng/µl) are loaded into a mini electrophoretic unit containing a global DNA analyzer (Agilent Bioanalyzer 2100, Santa Clara, Calif.). The analyzer either contains a fluorescent composition that binds to the DNA within the electrophoretic gel or one adds it to the analyzer. A graph comparing DNA fragment size (ranging from approximately 35 to approximately 10,380 bp) with fragment concentration is generated. Graphs of total DNA size from fresh and autoclaved cucumber DNA are compared. FIG. 12 illustrates the global measurement of total cucumber DNA before and after autoclave treatment. Number of base pairs (size) versus concentration (pg/ul) are compared. Fresh cucumber DNA ranges from <1,000 base pairs (bp) to approximately 10,000 bp. After autoclave treatment, total DNA is degraded and fragmented (<3,500 bp), sizes clustering between approximately 35 bp and approximately 400 bp. DNA integrity is the wholeness or completeness of a cell's genomic and organelle-based DNA. After heat treatments such as autoclaving, a cell's DNA integrity is reduced and this fragmentation can be measured globally. Based on the results, an algorithm which predicts time/temperature treatment based on global DNA fragmentation is generated. One uses can use this measurement of DNA integrity as a time/temperature integrator for inactivation of hazardous biological material in/on food matrices and/or medical devices.

Again, one can use extrinsic DNA or intrinsic DNA with this protocol for analyzing the DNA fragmentation.

Figure 13:
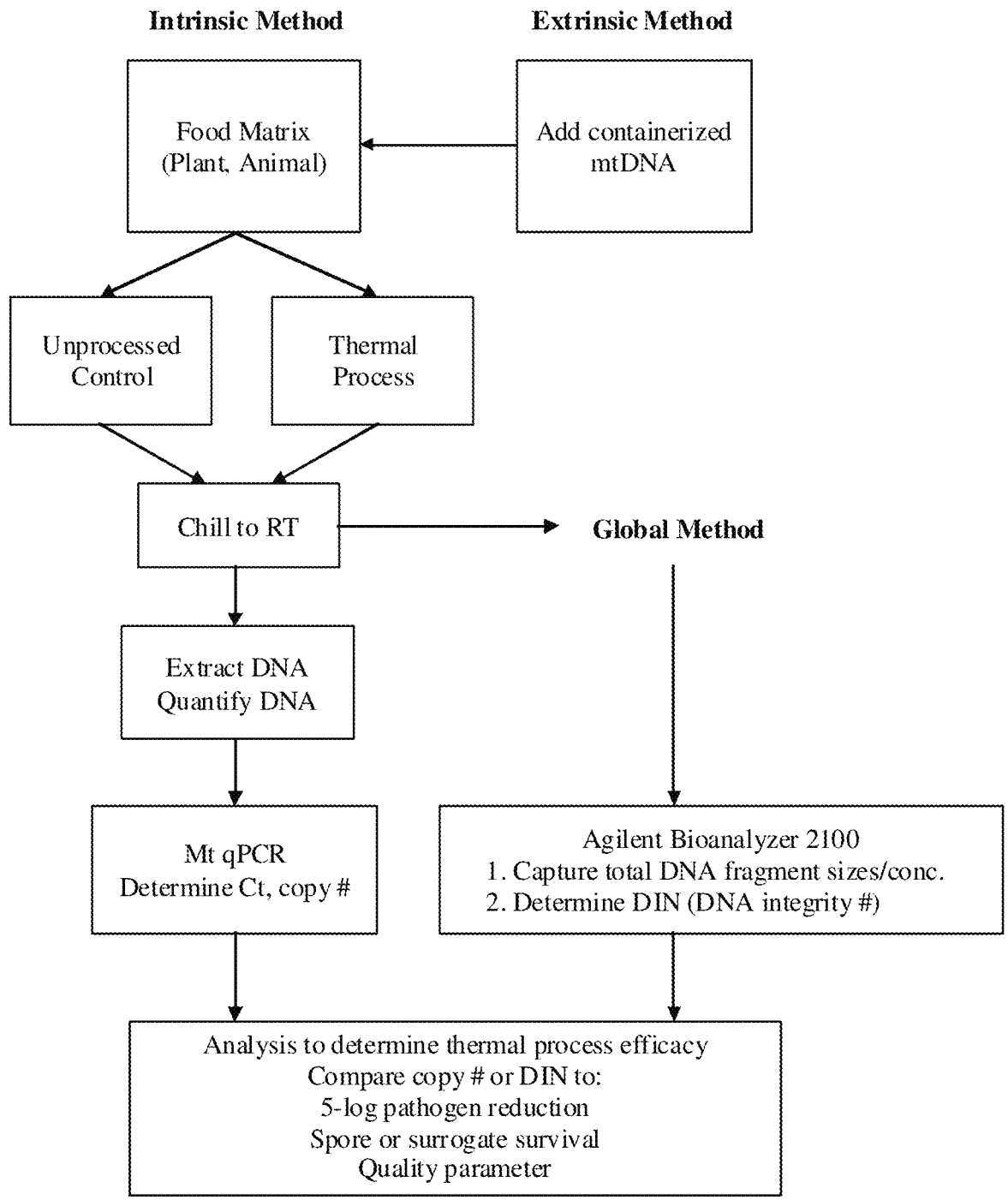
FIG. 13 is a flow chart illustrating the invention described herein.

A flow chart illustrating the methods of these novel time/temperature integrators of these inventions is in FIG. 13.

Figure 14A:
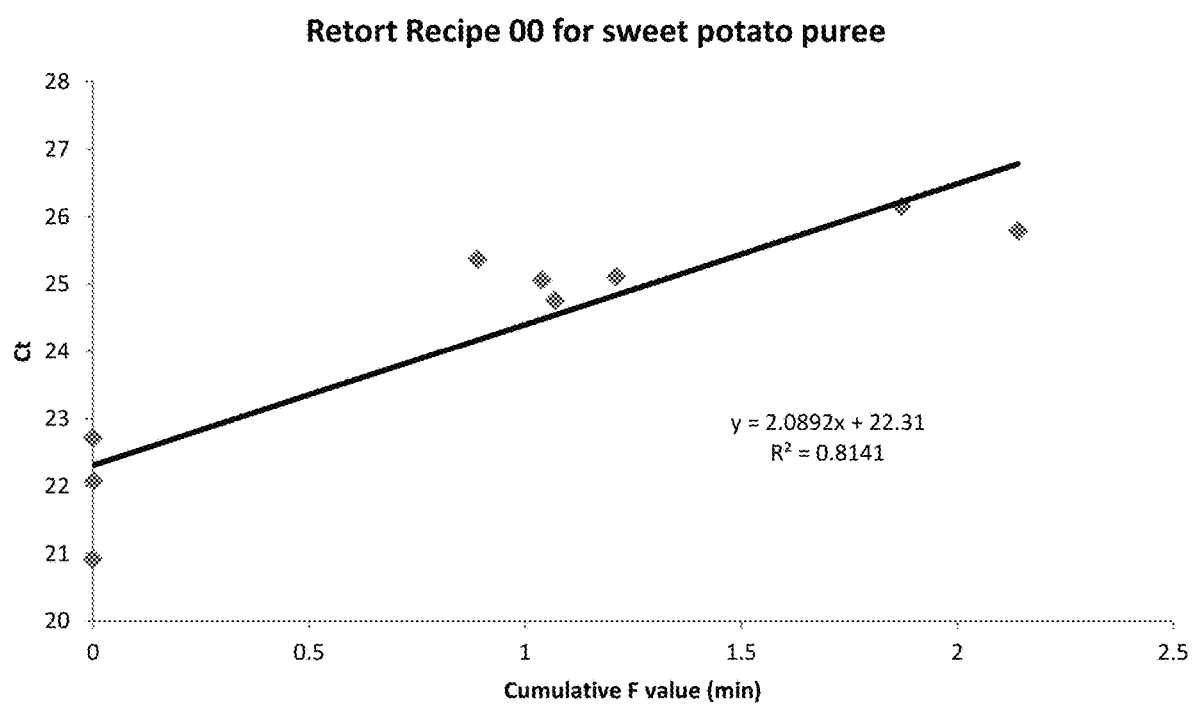
FIG. 14A illustrates the correlation between Ct values of sweet potato mtDNA and F values of inactivation of *G. stearothermophilus* in canned sweet potato using substandard 12-D protocol (protocol 00).
Figure 14B:
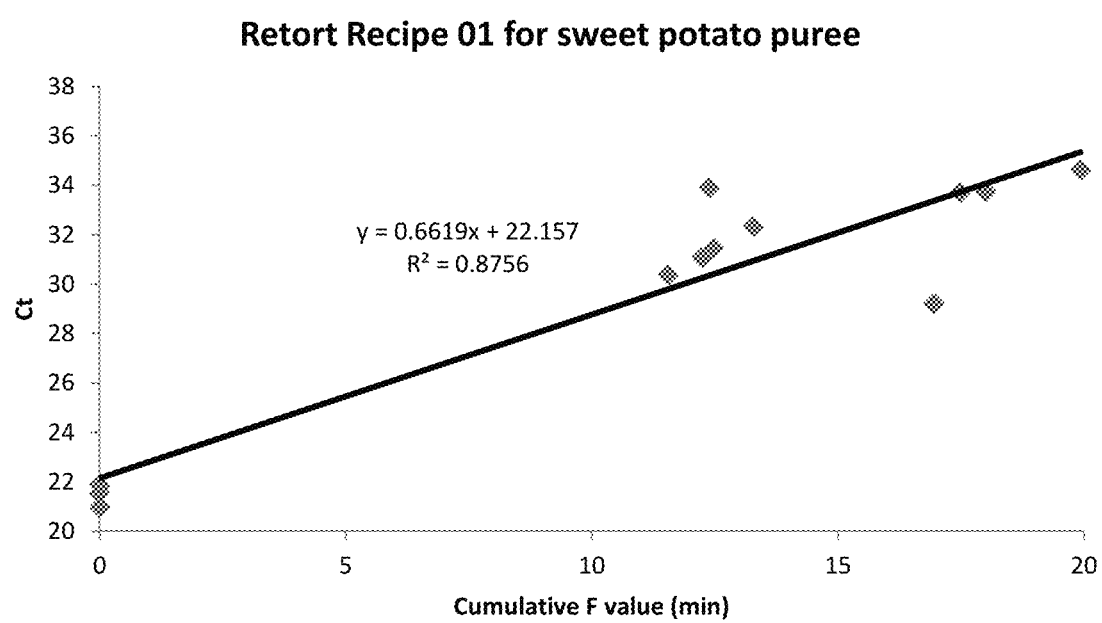
FIG. 14B illustrates the correlation between Ct values of sweet potato mtDNA and F values of inactivation of *G. stearothermophilus* in canned sweet potato using standard 12-D protocol (protocol 01).
Figure 15:
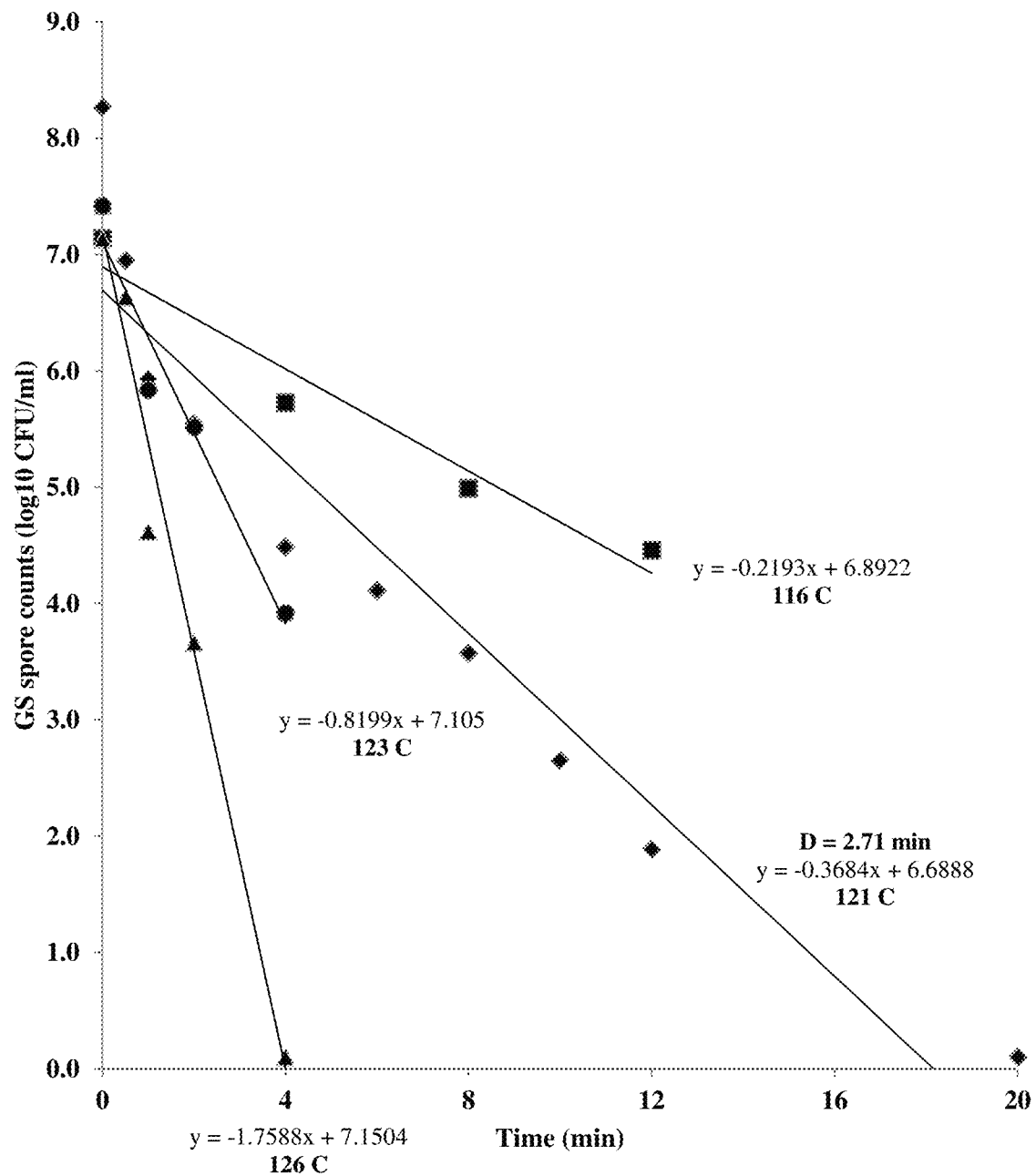
FIG. 15 illustrates the slopes used to calculate D values for timed oil bath treatments for *G. stearothermophilus* spores at 116° C., 121° C., 123° C., and 126° C. for the indicated times.
Figure 16:
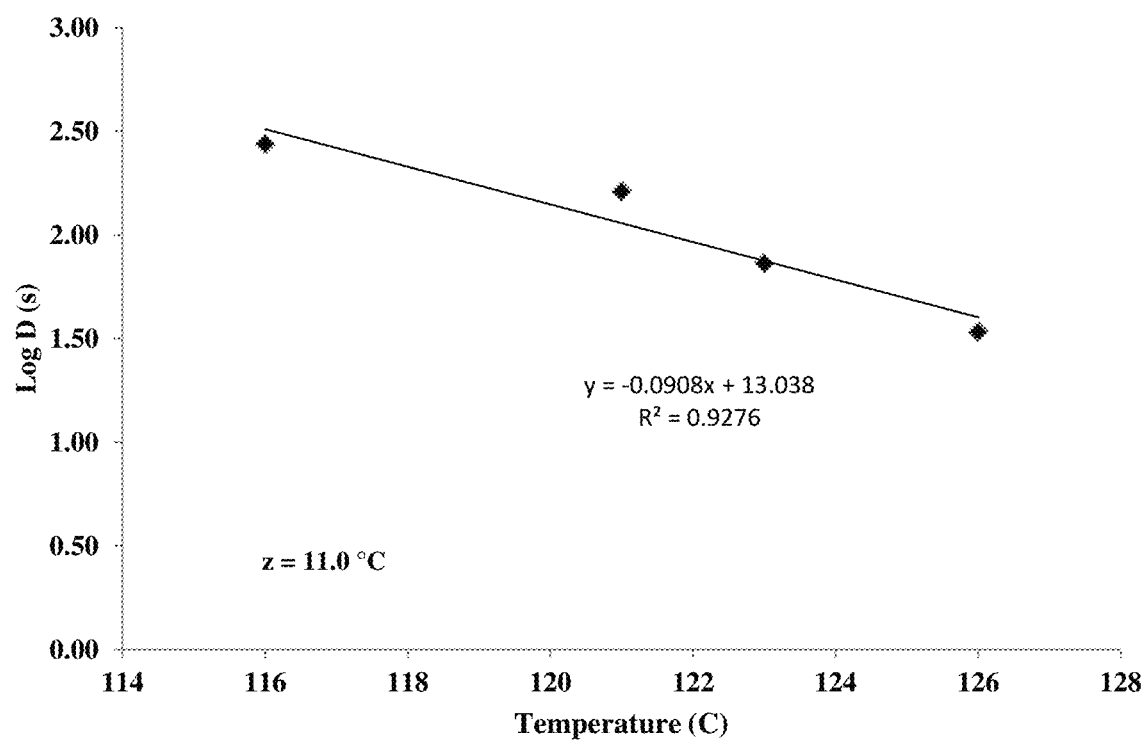
FIG. 16 illustrates the slope used to calculate the z-value for timed oil bath treatments for *G. stearothermophilus* spores at 116° C., 121° C., 123° C., and 126° C. for the indicated times.
Figure 17:
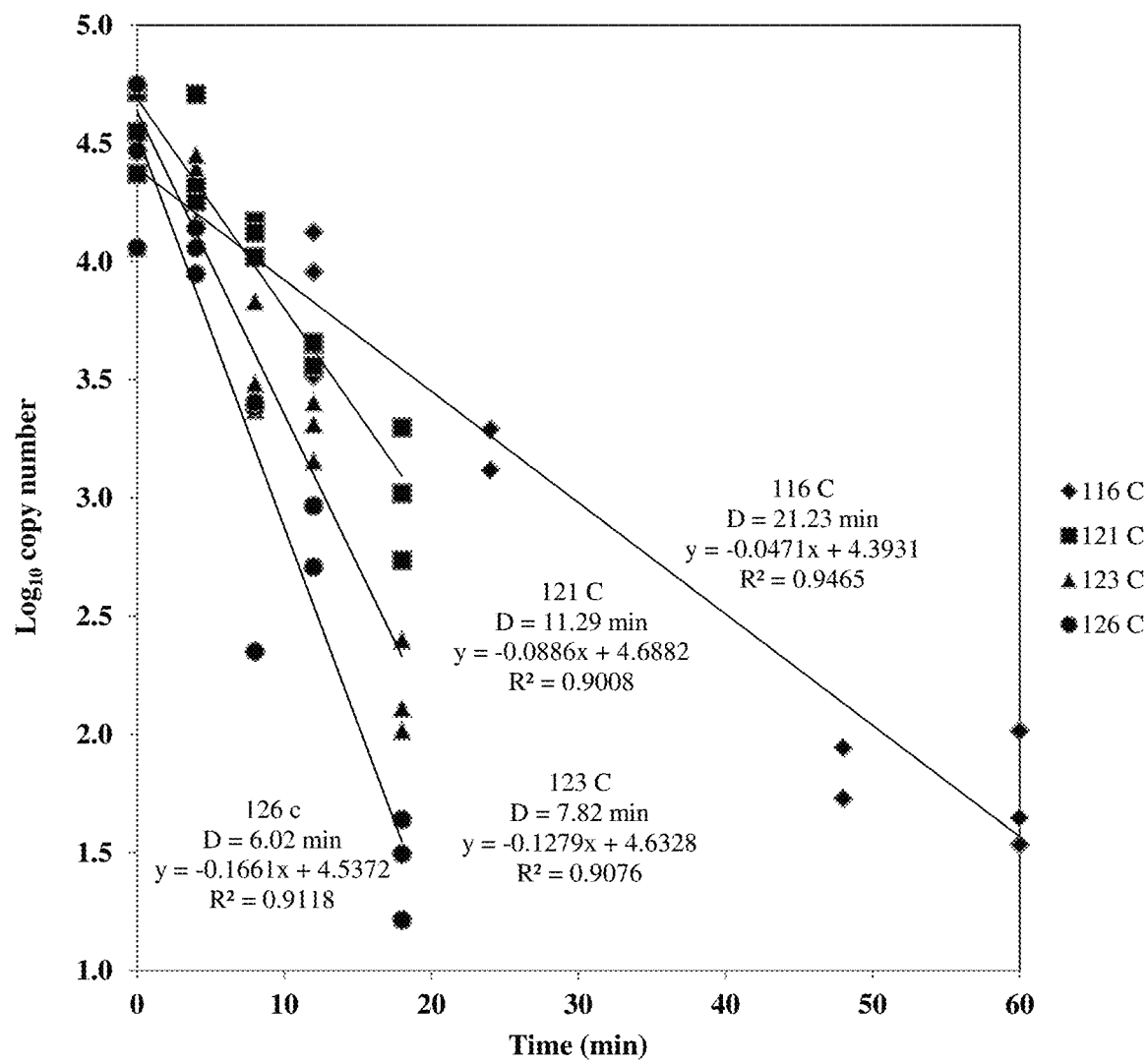
FIG. 17 illustrates sweet potato puree mtDNA fragmentation and D values in hot oil bath at 116° C., 121° C., 123° C., and 126° C. for the indicated times.
Figure 18:
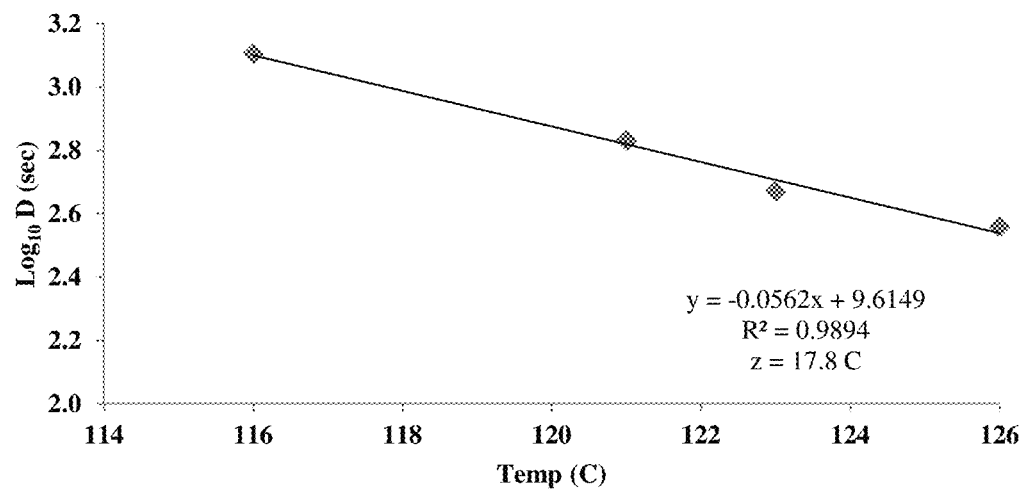
FIG. 18 illustrates the slope used to calculate z-value for sweet potato puree mtDNA fragmentation in hot oil bath at 116° C., 121° C., 123° C., and 126° C. for the indicated times.
Figure 19:
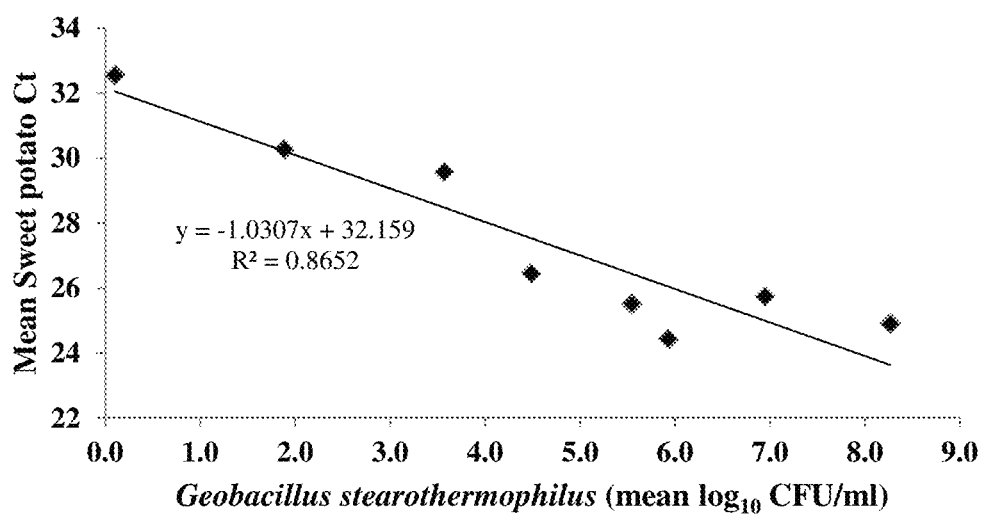
FIG. 19 illustrates the linear relationship between sweet potato puree mtDNA fragmentation in hot oil bath at 121° C. versus *G. stearothermophilus* spore counts in hot oil bath at 121° C.

Example 10 Comparison of Ct and F Values of Sweet Potato Puree with 12D-Retort Protocol Sweet potato puree is produced as described supra and placed in 68.3×101.6 mm cans outfitted with T-type C-2 tube and rod thermocouples (Ecklund-Harrison Technologies, Fort Myers, Fla.). Colorimetric *G. stearothermophilus* ampoules (Raven ProSpore; Mesa Laboratories, Inc., Lakewood, Colo.) are placed in the center of each can, adjacent to the thermocouple probes. Cans are sealed with a double seam using an automated can sealer (Dixie Canner Co., Athens, Ga.). Total weights of puree and size of head space are similar between all cans in each run. Canned sweet potato puree is loaded into a Model PR-900 pilot retort (Stock sterilisationstechnik, Hermanstock Maschf.; Neumunster, West Germany) with thermocouples attached to a recording device and run in one of two full water immersion protocols listed in Tables 3 and 4 infra. Protocol 00 (Table 3), sub-12D full water immersion, is a substandard treatment not meant to kill spores. Protocol 01 (Table 4), 12D full water immersion, is a 12D protocol meant to eliminate all *G. stearothermophilus* test spores. Each protocol is run in triplicate using three cans per run. Puree is sampled from the center of each can, the DNA is extracted, and the atp1 qPCR protocol performed as described supra using primers 174F and 174R. ProSpore ampoules are incubated at 55° C. for 48 hours as recommended by the supplier, and then assessed for colorimetric change. F values are determined from the thermal couple time-temperature data collected. F value is calculated as follows: $F=10^{(T-121.1/10)} \Delta t$; where T is temperature in ° C. and t is time in minutes. Ct values are correlated to F values of all 12D and sub-12D runs and are shown in FIG. 14A (protocol 00 which is shown in Table 3) and FIG. 14B (protocol 01 which is shown in Table 4). The protocols presented in Table 3 and Table 4 contain information provided by the manufacturer (Hermanstock Maschf.; Neumunster, West Germany). The results support the use of qPCR of mtDNA of a food product to assess bacterial spore inactivation, because the Ct values are highly correlated to F values.

TABLE 3

| Step | Temperature (F.) | Pressure (psi) | Time | Temp Gradient | Pressure Gradient |
|---|---|---|---|---|---|
| Heating Storage Vessel | 180 | 20 | — | — | — |
| Sterilization I (Vent) | 180 | 20 | 20 sec | — | — |
| Sterilization II (Come up) | 242 | 20 | 10 min | 10 | — |
| Sterilization III (Hold) | 242 | 20 | 35 min | — | — |
| Cooling 1 | — | 20 | 10 min | — | — |
| Cooling 2 | 90 | 10 | 20 min | — | 0.6 |
| Drain | 90 | — | 4 min | — | — |

TABLE 4

| Step | Temperature (F.) | Pressure (psi) | Time | Temp Gradient | Pressure Gradient |
|---|---|---|---|---|---|
| Heating Storage Vessel | 200 | 20 | — | — | — |
| Sterilization I (Vent) | 200 | 20 | 20 sec | — | — |
| Sterilization II (Come up) | 260 | 20 | 12 min | 10 | — |
| Sterilization III (Hold) | 260 | 20 | 35 min | — | — |
| Cooling 1 | — | 20 | 10 min | — | — |
| Cooling 2 | 90 | 10 | 12 min | — | 0.6 |
| Drain | 90 | — | 4 min | — | — |

Example 11 Comparison of Ct Value with D- and z-Values

In an effort to mimic and quantify values in a 12D thermal process, the kill curve of *G. stearothermophilus* (a *C. botulinum* surrogate) spores with resulting D- and z-values are compared to Ct values of sweet potato puree in a hot oil bath at the following temperatures: 116° C., 121° C., 123° C., and 126° C. A hot oil bath (Neslab Instruments, Newington, N.H.) filled with 8 L white mineral oil (Solutia, Inc, St. Louis, Mo.) is used to maintain each target temperature for substances placed in a thermal death tube (TDT). This system replicates conditions in an industrial retort, heat exchanger or microwave thermal process. The TDT is composed of a ¾ inch aluminum screw post (Screwpost.com, Muskegon, Mich.) cut to size and filed for smoothness, ¼ inch nylon machine screws, Viton fluoroelastomer O-ring gaskets (screw size #6) and Viton flat washers size #6 (McMaster-Carr, Atlanta, Ga.). Temperature is monitored using a type J-K-T microprocessor thermometer thermocouple (Omega Corp., Stamford, Conn.). Come up time (CUT) for TDTs is determined for all target temperatures. In each TDT, 100 μl of 1:4 diluted puree or 100 μl of *G. stearothermophilus* (GS) spores (approximately $10^8$ CFU/ml) are inserted and sealed. For GS spores, samples are heated for 0, 4, 8 and 12 minutes at 116° C.; for 0, 0.5, 1, 2, 4, 8, 16 and 20 minutes at 121° C.; for 0, 1, 2 and 4 minutes at 123° C.; and for 0, 0.5, 1, 2 and 4 minutes at 126° C., with all heat treatments beginning after come up time. Samples of diluted sweet potato puree are heated for 0, 12, 24, 48 and 60 minutes at 116° C.; for 0, 4, 8, 12 and 18 minutes at 121° C.; for 0, 4, 8, 12 and 18 minutes at 123° C.; and for 0, 4, 8, 12 and 18 minutes at 126° C.; with all heat treatments beginning after come up time. Three replications are run per time point; 3 TDTs are placed in a metal tea strainer to facilitate removal of samples from hot oil. Strainers containing TDTs are taken out of oil bath and immediately placed in an ice slurry for 30 second to quickly cool them. Strainers containing TDTs are stored at room temperature until ready for DNA extraction or culture plating. Total amount of sweet potato puree recovered from hot oil bath treatment is determined from an initial sample of 100 μl.

The D value (decimal reduction time) is defined as the time in minutes at a given temperature that results in a one log reduction in microbial count (Pflug, Irving, *Microbiology and Engineering of Sterilization Processes.* 7th Ed., published by Environmental Sterilization Laboratory; Minneapolis, Minn. (1990)). Using the equation:

$$N=N_0 10^{-t/D_T}$$

where $N_0$ and N are the initial and final number of microorganisms, respectively; the D value at a given temperature ($D_T$) is calculated by graphing the $\log_{10}$ number of microorganisms over time (minutes) and determining the slope: slope=−1/$D_T$.

The z-value is the temperature change required for a one log change in the D value of a microorganism (Pflug, Irvine supra (1990)). Using the equation $$D_T=D_{ref}10^{Tref-T/z}$$

the z-value is calculated by graphing log D value (seconds) versus temperature and determining the slope: slope=−1/z.

*G. stearothermophilus* spores are serially diluted and plated with on BHI agar (Becton Dickinson, Sparks, Md.) using a spiral plater (Spiral Biotech Inc., Norwood, Mass.) or a simplified agar plate technique (Jett, et al., *BioTechniques* 23:648-650 (1997)). After 24 hours incubation at 55° C., colonies are enumerated with an automated spiral plate counter (Spiral Biotech Inc., Norwood, Mass.) or counted manually. The lower detection limits are $4\times10^2$ and $1\times10^3$ CFU/ml for the spiral plate and simplified agar technique, respectively.

Ct values are converted to $\log_{10}$ copy numbers using the linear relationship determined empirically from the standard curve of the 174 bp amplicon:

$$y=-3.1909x+38.091$$

where y is the Ct value and x is the $\log_{10}$ copy number.

$D_{121}$ and z-values determined in hot oil bath for *G. stearothermophilus* spores are 2.71 minutes and 11.0° C. (see FIGS. 15 and 16), respectively. These values are slightly higher than values obtained using a commercial product with the same GS strain spores for autoclave validation (Prospore, Mesa Labs, Lakewood, Colo.) which cite a $D_{121}$ value of 1.8 minutes and a z-value of 7.4° C. under saturated steam. Prior art D and z-values for GS spores are $D_{120}$ from 1.5 to 3 minutes with z-value of greater than or equal to 6° C. (see www.namsa.com/Portals/O/Documents/*Geobacillus_stearothermophilus*-technical-info.pdf) and $D_{121}$ of approximately 2 minutes in water (Lundahl, G., *PDA J. Pharm. Sci. Technol.* 57:249-262 (2003)). Both of these cited values are based on an initial population of $10^6$ spores. Head, et al. (*J. Appl. Microbiol.* 104:1213-1220 (2007)) determined that D and z-values vary widely based on the initial concentration of spores ($10^3$ versus $10^6$) when treated with superheated steam. While the TDT employed herein is a pressurized container, one would not expect the same time-temperature treatment in a hot oil bath as pressurized, saturated stream in an autoclave. Based on precautionary notes in commercial spore technical data sheets (Prospore, Namsa, Northwood, Ohio) and values in the literature, spore D and z-values can vary widely because of the type of heat treatment (wet versus dry), initial concentration of spores, and spore carrier or media (Head, et al. (2007)). As an added precaution, a safety factor is added to empirically derived data, i.e. total death time is rounded up, to ensure complete destruction of spores (Tucker, et al., *History of the minimum botulinum cook for low-acid canned foods.* Campden & Chorleywood Food Research Association Group. R & D report no. 260. Doc Ref:FMT/REP/90194/1 (2008)).

$D_{121}$ and z-values for Ct values from a 174-bp universal plant amplicon are 11.3 minutes and 17.8° C. (see FIGS. 17 and 18), respectively, for mtDNA from sweet potato puree heated in a hot oil bath. The conversion of Ct to $\log_{10}$ copy number of amplicon results in the Ct-$D_{121}$ value (11.3 minutes) being much higher than the *G. stearothermophilus* $D_{121}$ (2.71 minutes). *G. stearothermophilus* spores have a $D_{121}$ value approximately 10× greater than *C. botulinum* ($D_{121}$=0.21 minutes; Esty & Meyer, *J. Infectious Dis.* 31:650-663 (1922); Townsend, et al., *Food Res.* 3:323-346 (1938); Stumbo, C. R., *Thermobacteriology in Food Processing*. 1st Ed. Academic Press 111 Fifth Ave, New York, N.Y. (1965)), the spore of concern in low acid, canned or aseptically-packaged foods. The Ct-$D_{121}$ value of sweet potato puree mtDNA is approximately 4× greater than the *G. stearothermophilus* indicator spore. Because of its higher $D_{121}$ value, it might be difficult to predict the FDA recommended F value for sterilization ($F_0$=5 minutes) using a log function of Ct value. However, sterilization in the pharmaceutical industry requires higher values ($F_0$>12 minutes) where GS spores leave no measurable outcome (Lundahl, G. (2003)).

When compared directly, the increase in Ct value has nearly a 1:1 ratio with *G. stearothermophilus* destruction at 121° C. in hot oil bath treatments (ratio=0.875) (FIG. 19). The destruction of mtDNA as measured by $\log_{10}$ copy number is not a first order relationship but a simple inverse relationship with time-temperature. Therefore, the use of Ct values directly will have greater utility than conversion to log values.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim:

1. A method for determining the amount of inactivation of hazardous biological material in a food matrix comprising:
   exposing intrinsic nucleic acid from said food matrix to a first polynucleotide, to a second polynucleotide, and optionally a label;
   amplifying said intrinsic nucleic acid using a DNA amplification method to produce an amplicon;
   determining the threshold cycle value of said amplified intrinsic nucleic acid; and
   comparing said threshold cycle value of said amplified intrinsic nucleic acid to known threshold cycle value of food material that is equivalent to desired amount of inactivation of said hazardous biological material; wherein the sequence of said amplicon at the amplicon's 5' end is at least 95% identical to the sequence of said first polynucleotide and the sequence of said amplicon at the amplicon's 3' end is at least 95% identical to the sequence of said second polynucleotide or the reverse complement thereof; wherein said first polynucleotide has a sequence of between approximately 15 contiguous bases to approximately 45 contiguous bases of SEQ ID NO: 9 and said second polynucleotide has a sequence of between approximately 15 contiguous bases to approximately 45 contiguous bases of the reverse complement of SEQ ID NO: 9; wherein the sequence of said amplicon is between approximately 80 bp and approximately 250 bp; and wherein said food matrix previously underwent an inactivation process.

2. The method of claim 1 wherein said label is selected from the group consisting of an intercalating dye, a fluorescent dye, a spectroscopic label, a photochemical label, a biochemical label, an immunochemical label, and a chemical label.

3. The method of claim 1 wherein said food matrix is obtained from plant or animal.

4. The method of claim 1 wherein said first polynucleotide has the sequence in SEQ ID NO: 1 and said second polynucleotide has the sequence in SEQ ID NO: 2 or the reverse complement thereof.

5. The method of claim 4 wherein said label is selected from the group consisting of an intercalating dye, a fluorescent dye, a spectroscopic label, a photochemical label, a biochemical label, an immunochemical label, and a chemical label.

6. The method of claim 1 wherein said first polynucleotide has the sequence in SEQ ID NO: 3 and said second polynucleotide has the sequence in SEQ ID NO: 4.

7. The method of claim 6 wherein said label is selected from the group consisting of an intercalating dye, a fluorescent dye, a spectroscopic label, a photochemical label, a biochemical label, an immunochemical label, and a chemical label.

8. The method of claim 1 wherein said first polynucleotide has the sequence in SEQ ID NO: 5 and said second polynucleotide has the sequence in SEQ ID NO: 6.

9. The method of claim 8 wherein said label is selected from the group consisting of an intercalating dye, a fluorescent dye, a spectroscopic label, a photochemical label, a biochemical label, an immunochemical label, and a chemical label.

10. The method of claim 1 wherein said first polynucleotide has the sequence in SEQ ID NO: 7 and said second polynucleotide has the sequence in SEQ ID NO: 8.

11. The method of claim 10 wherein said label is selected from the group consisting of an intercalating dye, a fluorescent dye, a spectroscopic label, a photochemical label, a biochemical label, an immunochemical label, and a chemical label.

12. A method for determining the efficacy of a protocol to inactivate hazardous biological material in a food matrix comprising:
    determining amount of intrinsic nucleic acid fragmentation in said food matrix after undergoing said protocol; wherein said intrinsic nucleic acid fragmentation determination step comprises
    exposing said intrinsic nucleic acid from said food matrix to a first polynucleotide and to a second polynucleotide, and optionally to a label;
    amplifying said intrinsic nucleic acid;
    determining a threshold cycle value of said amplified intrinsic nucleic acid, wherein said threshold cycle value identifies said amount of nucleic acid fragmentation in said food matrix; and
    comparing said amount of nucleic acid fragmentation in said food matrix to a known amount of nucleic acid fragmentation that is equivalent to desired amount of inactivation of said hazardous biological material; wherein said amplicon's length is between approximately 80 bp and approximately 250 bp; and wherein said first polynucleotide's sequence is between approximately 15 contiguous bases to approximately 45 contiguous bases of mtDNA; wherein said second polynucleotide's sequence is between approximately 15 contiguous bases to approximately 45 contiguous bases of said mtDNA; and wherein said first polynucleotide and said second polynucleotide bind to different strands of said intrinsic nucleic acid.

13. The method of claim 12 wherein said label is selected from the group consisting of an intercalating dye, a fluorescent dye, a spectroscopic label, a photochemical label, a biochemical label, an immunochemical label, and a chemical label.

14. The method of claim 12 wherein said food matrix is plant tissue or animal tissue.

15. A method for assessing the efficacy of an inactivation protocol to inactivate hazardous biological material in or on an item, said method comprising:
   determining amount of extrinsic nucleic acid fragmentation after subjecting said extrinsic nucleic acid to said inactivation protocol; wherein said extrinsic nucleic acid fragmentation determination step comprises
   exposing said extrinsic nucleic acid to a first polynucleotide, to a second polynucleotide, and optionally to a label;
   amplifying said extrinsic nucleic acid;
   determining a threshold cycle value of said amplified extrinsic nucleic acid, wherein said threshold cycle value identifies said amount of fragmentation of said extrinsic nucleic acid after undergoing said inactivation protocol; and
   comparing said amount of inactivated extrinsic nucleic acid fragmentation to a known amount of inactivated extrinsic nucleic acid fragmentation that is equivalent to desired amount of inactivation of said hazardous biological material; wherein said first polynucleotide's sequence and said second polynucleotide's sequence are located in said extrinsic nucleic acid such that said amplified extrinsic nucleic acid is between approximately 80 bp and approximately 250 bp; and wherein said first polynucleotide and said second polynucleotide bind to different strands of said amplified extrinsic nucleic acid.

16. The method of claim 15 wherein said label is selected from the group consisting of an intercalating dye, a fluorescent dye, a spectroscopic label, a photochemical label, a biochemical label, an immunochemical label, and a chemical label.

17. The method of claim 15 wherein said extrinsic nucleic acid is mtDNA.

18. The method of claim 17 wherein said mtDNA is atp1 or a fragment of atp1 of between approximately 80 bp and approximately 250 bp long.

19. The method of claim 17 wherein said mtDNA has a sequence of SEQ ID NO: 14, wherein said first polynucleotide has a sequence of SEQ ID NO: 1, wherein said second polynucleotide has a sequence of SEQ ID NO: 2, wherein said label is selected from the group consisting of an intercalating dye, a fluorescent dye, a spectroscopic label, a photochemical label, a biochemical label, an immunochemical label, and a chemical label.

20. The method of claim 17 wherein said mtDNA has a sequence of SEQ ID NO: 15, wherein said first polynucleotide has a sequence of SEQ ID NO: 3, wherein said second polynucleotide has a sequence of SEQ ID NO: 4, wherein said label is selected from the group consisting of an intercalating dye, a fluorescent dye, a spectroscopic label, a photochemical label, a biochemical label, an immunochemical label, and a chemical label.

21. The method of claim 17 wherein said mtDNA has a sequence of SEQ ID NO: 16, wherein said first polynucleotide has a sequence of SEQ ID NO: 5, wherein said second polynucleotide has a sequence of SEQ ID NO: 6, wherein said label is selected from the group consisting of an intercalating dye, a fluorescent dye, a spectroscopic label, a photochemical label, a biochemical label, an immunochemical label, and a chemical label.

22. The method of claim 17 wherein said mtDNA has a sequence of SEQ ID NO: 17, wherein said first polynucleotide has a sequence of SEQ ID NO: 7, wherein said second polynucleotide has a sequence of SEQ ID NO: 8, wherein said label is selected from the group consisting of an intercalating dye, a fluorescent dye, a spectroscopic label, a photochemical label, a biochemical label, an immunochemical label, and a chemical label.

23. A quality control method for hazardous biological material inactivation in or on an item comprising:
   processing a sample containing nucleic acid according to a predetermined inactivation protocol that causes said nucleic acid to degrade; wherein said sample contains either intrinsic nucleic acid or extrinsic nucleic acid;
   optionally, isolating said degraded nucleic acid, exposing said degraded nucleic acid to a first polynucleotide, a second polynucleotide, and optionally a label;
   amplifying said degraded nucleic acid using an amplification method to produce an amplicon of said degraded nucleic acid;
   determining the threshold cycle value of said amplified degraded nucleic acid; and
   comparing said threshold cycle value to a known threshold cycle value of nucleic acid that is equivalent to the desired amount of degradation of nucleic acid, wherein said nucleic acid degradation indicates said inactivation of said hazardous biological material; wherein the sequence of said first polynucleotide and the sequence of said second polynucleotide are located in said degraded nucleic acid such that the length of said amplicon is between approximately 80 bp and approximately 250 bp; and wherein said first polynucleotide and said second polynucleotide bind to different strands of said degraded nucleic acid.

24. The method of claim 23 wherein said label is selected from the group consisting of an intercalating dye, fluorescent dye, a spectroscopic label, a photochemical label, a biochemical label, an immunochemical label, and a chemical label.

25. The method of claim 23 wherein said nucleic acid is mtDNA.

26. The method of claim 25 wherein said mtDNA is atp1 or a fragment of atp1 between approximately 80 bp and approximately 250 bp long.

27. A quality control method for hazardous biological material inactivation comprising:
   processing a sample containing an organism's genomic nucleic acid according to a pre-determined inactivation method; wherein said sample contains either intrinsic genomic nucleic acid or extrinsic genomic nucleic acid; and wherein said inactivation method degrades said genomic nucleic;
   isolating said degraded genomic nucleic acid;
   running said degraded genomic nucleic acid on an electrophoretic gel;

determining the amount of nucleic acid fragmentation for nucleic acid sizes ranging from approximately 35 bp to approximately 10,380 bp;

determining the nucleic acid integrity number; and comparing said nucleic acid integrity number to a known nucleic acid integrity number that is equivalent to a desired amount of inactivation of said hazardous biological material; wherein said nucleic acid integrity number represents said sample's nucleic acid fragmentation and thus said hazardous biological material's inability to live after said processing.

* * * * *

SEQUENCE LISTING

```
<160> NUMBER OF SEQ ID NOS: 17

<210> SEQ ID NO 1
<211> LENGTH: 24
<212> TYPE: DNA
<213> ORGANISM: Ipomoea batatas

<400> SEQUENCE: 1
tttccgcgat aatggaatgc acgc                                   24

<210> SEQ ID NO 2
<211> LENGTH: 24
<212> TYPE: DNA
<213> ORGANISM: Ipomoea batatas

<400> SEQUENCE: 2
tccgatcgtt tagccgctct ttct                                   24

<210> SEQ ID NO 3
<211> LENGTH: 24
<212> TYPE: DNA
<213> ORGANISM: Ipomoea batatas

<400> SEQUENCE: 3
cgcctttgct caatttggct caga                                   24

<210> SEQ ID NO 4
<211> LENGTH: 24
<212> TYPE: DNA
<213> ORGANISM: Ipomoea batatas

<400> SEQUENCE: 4
ggcagtggtg catattgtgg ttgt                                   24

<210> SEQ ID NO 5
<211> LENGTH: 24
<212> TYPE: DNA
<213> ORGANISM: Ipomoea batatas
```

```
<400> SEQUENCE: 5
cgcctttgct caatttggct caga                                         24

<210> SEQ ID NO 6
<211> LENGTH: 24
<212> TYPE: DNA
<213> ORGANISM: Ipomoea batatas

<400> SEQUENCE: 6
agtacttctg tcagccttgc acct                                         24

<210> SEQ ID NO 7
<211> LENGTH: 24
<212> TYPE: DNA
<213> ORGANISM: Ipomoea batatas

<400> SEQUENCE: 7
gaatttgcca gcggtgtgaa agga                                         24

<210> SEQ ID NO 8
<211> LENGTH: 24
<212> TYPE: DNA
<213> ORGANISM: Ipomoea batatas

<400> SEQUENCE: 8
tcccgcagga acatccacaa taga                                         24

<210> SEQ ID NO 9
<211> LENGTH: 1293
<212> TYPE: DNA
<213> ORGANISM: Ipomoea batatas

<400> SEQUENCE: 9
tggatgagat cggtcgagtg gtctcagttg gagatgggat tgcacgtgtt tatggattga    60
acgagattca agctggggaa atggtggaat ttgccagcgg tgtgaaagga atagccttga   120
atcttgagaa tgagaatgta gggattgttg tctttggtag tgatactgct attaaggaag   180
gagatcttgt caagcgcact ggatctattg tggatgttcc tgcgggaaag gctatgctag   240
ggcgtgtggt cgacgccttg ggagtaccta ttgatggaag aggggctcta agcgatcacg   300
agcgaagacg tgtcgaagtg aaagcccctg ggattattga acgtaaatct gtgcacgagc   360
ctatgcaaac agggttaaaa gcggtagata gcctggttcc tataggtcgt ggtcaacgag   420
aacttataat cggagaccga caaactggaa aaacagctat tgctatcgat accatattaa   480
accaaaagca actgaactca agggcctcct ctgagagtga gacattgtat tgtgtctatg   540
tagcgattgg acagaaacgc tcaactgtgg cacaattagt tcaaattctt tcagaagcga   600
atgctttgga atattccatt cttgtagcag ccaccgcttc ggatcctgct cctctgcaat   660
ttttggcccc atattctggg tgtgccatgg gggaatattt ccgcgataat ggaatgcacg   720
cattaataat ctatgatgat cttagtaaac aggcggtagc atatcgacaa atgtcattat   780
tgttacgccg accaccaggt cgtgaggctt cccagggga tgttttttat ttacattccc    840
gtctcttaga aagagcggct aaacgatcgg accagacagg cgcaggtagc ttgaccgcct   900
tacccgtcat tgaaacacaa gctggagacg tatcggccta tattcccacc aatgtgatcc   960
ccattactga tggacaaatc tgtttggaaa cagagctctt ttatcgcgga attagacctg  1020
ctattaacgt cggcttatct gtcagtcgcg tcgggtctgc cgctcagttg aaagctatga  1080
```

```
aacaagtctg cggtagttta aaactggaat tggcacaata tcgcgaagtg gccgcctttg    1140
ctcaatttgg ctcagacctt gatgcagcga ctcaggcatt actcaataga ggtgcaaggc    1200
tgacagaagt actgaaacaa ccacaatatg caccactgcc aattgaaaaa caaattctag    1260
taatttatgc agctgtcaat ggattctgtg atc                                 1293

<210> SEQ ID NO 10
<211> LENGTH: 24
<212> TYPE: DNA
<213> ORGANISM: Ipomoea batatas

<400> SEQUENCE: 10
agaaagagcg gctaaacgat cgga                                           24

<210> SEQ ID NO 11
<211> LENGTH: 24
<212> TYPE: DNA
<213> ORGANISM: Ipomoea batatas

<400> SEQUENCE: 11
acaaccacaa tatgcaccac tgcc                                           24

<210> SEQ ID NO 12
<211> LENGTH: 24
<212> TYPE: DNA
<213> ORGANISM: Ipomoea batatas

<400> SEQUENCE: 12
aggtgcaagg ctgacagaag tact                                           24

<210> SEQ ID NO 13
<211> LENGTH: 24
<212> TYPE: DNA
<213> ORGANISM: Ipomoea batatas

<400> SEQUENCE: 13
tctattgtgg atgttcctgc ggga                                           24

<210> SEQ ID NO 14
<211> LENGTH: 174
<212> TYPE: DNA
<213> ORGANISM: Ipomoea batatas

<400> SEQUENCE: 14
tttccgcgat aatggaatgc acgcattaat aatctatgat gatcttagta aacaggcggt    60
agcatatcga caaatgtcat tattgttacg ccgaccacca ggtcgtgagg ctttcccagg    120
ggatgttttt tatttacatt cccgtctctt agaaagagcg gctaaacgat cgga          174

<210> SEQ ID NO 15
<211> LENGTH: 108
<212> TYPE: DNA
<213> ORGANISM: Ipomoea batatas

<400> SEQUENCE: 15
cgcctttgct caatttggct cagaccttga tgcagcgact caggcattac tcaatagagg    60
tgcaaggctg acagaagtac tgaaacaacc acaatatgca ccactgcc                 108

<210> SEQ ID NO 16
<211> LENGTH: 81
<212> TYPE: DNA
<213> ORGANISM: Ipomoea batatas
```

-continued

```
<400> SEQUENCE: 16
cgcctttgct caatttggct cagaccttga tgcagcgact caggcattac tcaatagagg      60
tgcaaggctg acagaagtac t                                               81

<210> SEQ ID NO 17
<211> LENGTH: 141
<212> TYPE: DNA
<213> ORGANISM: Ipomoea batatas

<400> SEQUENCE: 17
gaatttgcca gcggtgtgaa aggaatagcc ttgaatcttg agaatgagaa tgtagggatt      60
gttgtctttg gtagtgatac tgctattaag gaaggagatc ttgtcaagcg cactggatct     120
attgtggatg ttcctgcggg a                                              141
```